United States Patent [19]

Spears et al.

[11] Patent Number: 5,376,658
[45] Date of Patent: Dec. 27, 1994

[54] 5,10-METHYLENE-TETRAHYDROFOLATE AS A MODULATOR OF A CHEMOTHERAPEUTIC AGENT

[75] Inventors: Colin P. Spears, Glendale, Calif.; Bengt G. Gustavsson, Gothenburg, Sweden

[73] Assignee: University of Southern California, Los Angeles, Calif.

[21] Appl. No.: 174,571

[22] Filed: Dec. 23, 1993

Related U.S. Application Data

[63] Continuation of Ser. No. 789,729, Nov. 12, 1991, abandoned, which is a continuation-in-part of Ser. No. 521,712, May 11, 1990, abandoned.

[51] Int. Cl.$^5$ .................... A61K 31/505; A61K 49/00
[52] U.S. Cl. ........................................ 514/274; 424/10
[58] Field of Search ........................................ 514/274

[56] References Cited

PUBLICATIONS

Bunni, et al., "Accumulation of Tetrahydrofolates in Human Plasma After Leucovorin Administration", *Cancer Chemother Pharmacol.*, 23:353–57 (1989).
Caldwell, et al., "An Inexpensive Apparatus Facilitating the Storage of Oxygen Sensitive Compounds", *Prep. Biochem.*, 3:323–26 (1973).
Daron, et al., "A Kinetic Study of Thymidylate Synthase From Lactobacillus Casei", *J. Biol. Chem.*, vol. 253, No. 3, 940–45 (1978).
Davis, et al., "Modulation of 5-Fluoro-2'-Deoxyuridine Response By Folinic Acid In Human Colonic Tumor Cell Lines: The Role of Thymidylate Synthase", *Mol. Pharmacol.* 35:422–27 (1989).
Doroshow, et al., "Preliminary Analysis of a Randomized Comparison of 5-Fluorouracil Versus 5--Fluorouracil and High-Dose Continous-Infusion Folinic Acid in Disseminated Colorectal Cancer", *NCI Monogr.*, 5:171–74 (1987).
Douglas, "The Thymidylate Synthesis Cycle and Anticancer Drugs", *Medicinal Res. Rev.*, vol. 7, No. 4, 441–75 (1987).
Farina, et al., "Stereoselective Chemical Reduction of 5,10-Methenyltetrahydrofolate", *J. Am. Chem. Soc.*, 95:5409–11 (1973).
Glazer, et al., "Association of Cell Lethality With Incorporation of 5-Fluorouracil and 5-Fluorouridine Into Nuclear RNA in Human Colon Carcinoma Cells in Culture", *Mol. Pharmacol.*, 21: 468–73 (1982).
Goulian, et al., "Mechanism of Thymineless Death", *Adv. Exp. Med. Biol.*, 195:89–95 (1986).
Green, et al., "Examination of the Role of Methylenetetrahydrofolate Reductase in Incorporation of Methyltetrahydrofolate Into Cellular Metabolism", *FASEB J.*, 2:42–44 (1988).
Green, et al., "Substrate Flux Through Methylenetetrahydrofolate Dehydrogenase: Predicted Effects of the Concentration of Methylenetetrahydrofolate on Its Partitioning Into Pathways Leading to Nucleotide Biosynthesis or Methionine Regeneration", *Biochem.*, 27:8014–22 (1988).
Grem, et al., "Overview of Current Status and Future Direction of Clinical Trial With 5-Fluorouracil in Combination With Folinic Acid", *Cancer Treat. Rep.*, vol. 71, No. 12, 1249–64 (1987).
Horne, et al., "Vitamins and Coenzymes", *Methods in Enzymology*, 66:545–47 (1980) Enzymic Synthesis of (d)-L-5-Methyltetrahydropteroylglutamate.
Horwitz, et al., "Diastereoisomers of Formaldehyde Derivatives of Tetrahydrofolic Acid and Tetrahydroaminopterin", *J. Med. Chem.*, 12:49–51 (1969).

(List continued on next page.)

*Primary Examiner*—Marianne M. Cintins
*Assistant Examiner*—T. J. Criares
*Attorney, Agent, or Firm*—Robbins, Berliner & Carson

[57] ABSTRACT

The present invention relates to the compound 5,10-methylene-tetrahydrofolate ($CH_2FH_4$), and its solution product isomer $FH_4$, therapeutic uses of these compounds, and compositions thereof. $CH_2FH_4$ and $FH_4$ strongly modulate the in vivo antitumor effects of 5-Fluorouracil.

26 Claims, 5 Drawing Sheets

PUBLICATIONS

Houghton, et al., "Characterization of the Pools of 5,10-Methylenetetrahydrofolates and Tetrahydrofolates in Xenografts of Human Colon Adenocarcinoma", *Cancer Research*, 48:3062-69 (1988).

Hughes, Chemical Abstracts 10:95797 (1989), corresponding to European Patent Application No. 284,338.

Kallen, "The Dissociation Constants of tetrahydrofolic Acid", *J. Biol. Chem.*, vol. 241, No. 24, 5845-50, 5851-5863 (1966).

Kallen, "Tetrahydrofolic Acid And Formaldehyde", *Methods in Enzymology*, vol. 18, Part B, 705-16 (1971).

Kaufmanm, et al., "Chromatographic Separation of the Diastereoisomers of DL, L-5, 10-Methylenetetrahydrofolate", *J. Biol. Chem.*, 238:1498-1500 (1963).

Keyomarsi, et al., "Mechanism of the Cytotoxic Synergism of Fluoropyrimidines and Folinic Acid in Mouse Leukemic Cells", *J. Biol. Chem.*, vol. 263, No. 28 14402-09 (1988).

Kisliuk, et al., "Polyglutamyl Derivatives of Folate as Substrates and Inhibitor of Thymidylate Synthestase", *J. Biol. Chem.*, vol. 249, No. 13, 4100-03 (1974).

Kisliuk, et al., "Polyglutamyl Derivatives of Tetrahydrofolate as Substrates For Lactobacillus Casfi Thymidylate Synthase", *Biochem.*, 20:929-934 (1981).

Kufe, et al., "5-Fluorouracil Incorporation Into Human Breast Carcinoma RNA Correlates With Cytotoxicity", *J. Biol. Chem.*, vol. 256, No. 19, 9802-05 (1931).

Lockshin, et al., "Biochemical Factors Affecting the Tightness of 5-Fluorodeoxyuridylate Binding to Human Thymidylate Synthetase", *Biochem. Pharmacol.*, 30:247-57 (1981).

Machover, et al., "Treatment of Advanced Colorectal and Gastric Adenocarcinomas With 5-FU Combined With High-Done Folinic Acid: A Pilot Study", *Cancer Treat. Rep.*, vol. 66, No. 10, 1803-07 (1982).

Mathews, et al., "Enzymic Preparation of the L,L--Diastereoisomer of Tetrahydrofolic Acid", *J. Biol. Chem.*, vol. 235, No. 11, 3304-08 (1960).

Matthews, et al., "Folypolyglutamates as Substrates and Inhibitors of Folate-Dependent Enzymes", *Adv. Enz. Regul.*, 26:157-70 (1987).

Moran, et al., "biochemical Determinants of Tumor Sensitivity to 5-Fluorouracil Ultrasensitive Methods for the Determination of 5-Fluor-2'-Deoxyuridylate,2-'-Deoxyuridylatem, and Thymidylate Synthetase", *Proc. Natl. Acad. Sci. USA*, vol. 76, No. 3, 1456-60 (1979).

Nash, "The Colorimetric Estimation of Formaldehyde by Means of the Hantzsch Reaction", *Biochem. J.*, 55:416-21 (1953).

Poe et al., "4, 10-Methylene-5,6,7,8-Tetrahydrofolate. Conformation of the Tetrahydropyrazine and Imidazolidine Rings", *Biochem.*, 18:5527-30 (1979).

Poon et al., "Biochemical Modulation of Fluorouracil: Evidence of Significant Improvement of Survival and Quality of Life in Patients with Advanced Colorectal Carcinoma", *J. Clin. Oncol.*, vol. 7, No. 10 1407-18 (1989).

Reddy et al., "Multienzyme Complex For Metabolic Channeling in Mammalian DNA Replication", *Proc. Natl. Acad. Sci.*, 77:3312-16 (1980).

Santi, et al., "Kinetics and Thermodynamics of the Interaction of 5-Fluoro-2'-Deoxyuridylate With Thymidylate Synthase", *Biochem.*, 26:8606-13 (1987).

Sato, et al., "Preparation of (6R)-Tetrahydrofolic Acid and (6R)-5-Formyltetrahydrofolic Acid of High Stereochemical Purity", *Analytical Biochemistry*, 154:516-24 (1986).

Schirch, et al., "Interaction of Folylpolyglutamates With Enzymes in One-Carbon Metabolism", *Arch. Biochem. Biophys.*, 269:371-80 (1989).

Spears, et al., "In Vivo Kinetics of Thymidylate Synthetase Inhibition in 5-Fluorouracil-Sensitive and -Resistant Murine Colon Adenocarcinomas", *Cancer Res.*, 42:450-56 (1982).

Spears, "Thymidylate Synthetase Inhibition in Peyton Adenocarcinoma Xenografts Following Bolus 5--Fluorouracil", *Exerpta Med.*, 647:12-19 (1984).

Spears, et al., "Assay and Time Course of 5--Fluorouracil Incorporation Into RNA of L110/0 Ascites Cells in Vivo", *Molecular Pharmacology*, 27:302-07 (1985).

Spears, et al., "Methods for Thymidylate Synthase Pharmacodynamics: Serial Biopsy, Free and Total TS, FdUMP and dUMP, and H4PTEGLU and CH2-H4-PTEGLU Assays", *Adv. Exp. Med. Biol.*, 244:98-104 (1988).

Spears, et al., "Folinic Acid Modulation of Fluorouracil: Tissue Kinetics of Bolus Administration", *Invest New Drugs*, 7:27-36 (1989).

PUBLICATIONS

Spears, et al., "Activation of Leucovorin (CF) to Methylene-Tetrahydrofolate ($CH_2FH_4$) for Improving Thymidylate Synthase (TS) Inhibition After 5-FU: Effects of CF Dose, L-Serine, L-Glutamate, and Direct Methyl-Tetrahydrofolate ($CH_3FH_4$) Administration", *Proc. Am. Soc. Clin. Oncol.*, 8:69 (1989).

Spears, et al., "Deoxyuridylate Effects on Thymidylate Synthase-5-Fluoro-Deoxyuridylate-Folate Ternary Complex Formation", *Biochem. Pharmacol.*, vol. 38, No. 18, 2985-93 (1989).

Sur, et al., "Response of Methylenetetrahydrofolate Levels To Methotrexate in Krebs Ascites Cells", *Biochem. J.*, 216:295-98 (1983).

Swain, et al., "Fluorouracil and High-Dose Leucovorin in Previously Treated Patients With Metastatic Breast Cancer", *J. Clin. Ocol.*, vol. 7, No. 7 890-99 (1989).

Temple, Jr., et al., "Chemical and Physical Properties of Folic Acid and Reduced Derivatives", *Folates and Pterins*, 61-63, 93-120 (1984).

Trave, et al., "Plasma and Tumor Tissue Pharmacology of High-Dose Intravenous Leucovorin Calcium in Combination With Fluorouracil in Patients With Advanced Colorectal Carcinoma", *J. Clin. Oncol.*, vol. 6, No. 7, 1184-1191 (1988).

von R Kalbermatten, et al., "$^{13}$C-UND $^{15}$N-NMR.-Spektroskopische Unterschungen An Der (6RS)-5, 10-Methylen-5,6,7,8-Tetrahydro-L-Folsaure$^2$); Eindeutiger Beweis Ihrer Struktur", *Helv. Chim. Acta.*, 64: 2627-35 (1988).

Wood, et al., Chemical Abstracts 109:93606j (1988), corresponding to European Patent Application (266,042).

Wright, et al., "Selective Expansion of 5, 10-Methylenetetrahydrofolate Pools and Modulation of 5-Fluorouracil Antitumor Activity by Leucovorin In Vivo", *Cancer Res.*, 49:2592-96 (1989).

Zakrzewski, "Evidence for the Chemical Interaction Between 2-Mercaptoethanol and Tetrahydrofolate", *J. Biol. Chem.*, vol. 241, No. 12, 2957-61 (1966).

Zakrewski, et al., "A New Preparation of Tetrahydrofolic Acid", *Methods Enzymol.*, vol. 18, Part B, 728-31 (1971).

(6R,S)-METHYLENE-TETRAHYDROFOLIC ACID OR CH2FH4

CONFIGURATION OF THE NATURAL (6R)-CH2FH4 ENANTIOMER

5,10-METHYLENE-TETRAHYDROFOLATE AS A MODULATOR OF A CHEMOTHERAPEUTIC AGENT

This is a continuation of Ser. No. 07/789,729 filed Nov. 12, 1991, now abandoned, which in turn is a continuation-in-part of Ser. No. 07/521,712 filed May 11, 1990, now abandoned.

BACKGROUND OF THE INVENTION

1. Technical Field

The subject matter of the present invention relates to 5,10-methylene-tetrahydrofolate ($CH_2FH_4$), therapeutic uses of this compound and compositions thereof. $CH_2FH_4$ strongly modulates the in vivo antitumor effects of 5-Fluorouracil. Furthermore, the present invention additionally relates to a solution product isomer of $CH_2FH_4$, tetrahydrofolate ($FH_4$), which also strongly modulates the in vivo antitumor effects of 5-Fluorouracil. $CH_2FH_4$ and $FH_4$ both exist in a natural ((6R)-$CH_2FH_4$ and (6S)-$FH_4$) and unnatural ((6S)-$CH_2FH_4$ and (6R)-$FH_4$) diastereomeric form and both forms may be utilized for purposes of the present invention. In solution, $CH_2FH_4$ and $FH_4$ exist in chemical equilibrium, with requirements for millimolar formaldehyde concentrations to favor the balance toward $CH_2FH_4$.

2. Background Information

The compound 5-Fluorouracil (5-FU) is possibly the most widely used anticancer drug in the world. In the 1970s and early 1980s, the prevailing opinion among cancer researchers was that the key biochemical lesion caused by 5-FU in tumor cells resulted from the drug's incorporation into RNA (Kufe et al., *J. Biol. Chem.* 256:9802 (1981) and Glazer et al., *Mol. Pharmacol.* 21:468 (1982)).

In 1982, using a specifically designed assay of the DNA enzyme, thymidylate synthase (TS) (EC 2.1.1.45), the present inventors established that the therapeutic mechanism of 5-FU against murine colon cancer was complete inhibition of TS or abrogation of TS activity (Spears et al., *Cancer Res.* 42:450–56 (1982)). In fact, the present inventors were the first to report a clinical correlation between TS level in a patient's cancer after 5-FU treatment and response (Spears et al., *Cancer Res.* 44:4144–50 (1984)). The finding has been confirmed by several research groups.

TS is the only intracellular source of new ("de novo") thymine synthesis, as the enzyme which catalyzes the methylation of deoxyuridylate to form thymidylate (thymine-2'-deoxyribose-5'-phosphate). Thymine is one of the four main building blocks of DNA, and its occurrence in DNA (vs. its absence in RNA) is the major structural difference between DNA and RNA. Thus, the activity of TS to make new thymidylate and DNA is essential to cell division, tissue regeneration and turnover, and tumor growth. The source of the methyl one-carbon group for synthesis of thymidylate is $CH_2FH_4$ and its polyglutamates. The mechanism of methyl transfer by TS has recently been reviewed (K. T. Douglas, *Medicinal Res. Rev.* 7:441–75 (1987)). After initial weak binding of deoxyuridylate to TS, the enzyme catalyzes ring-opening of $CH_2FH_4$ at the imidazole C11 ring. This may be the rate limiting step overall. The relative stability of tetrahydrofolate within the ternary complex, toward oxidation, suggests that the ring-opening occurs with the substitution at N5, in accordance with formation of an N5-iminium cation species (S. J. Benkovic, *Ann. Rev. Biochem.*, 49:227–51 (1980)). Covalent bonding between the methylene group and the C5-position of deoxyuridylate is accompanied by rapid hydride transfer from the C6-position of the ring-opened $CH_2FH_4$ so that CH3- is formed on the C5 position of the nucleotide. This leads rapidly to expulsion of the two products from the TS binding site(s), i.e., thymidylate and dihydrofolate. TS is the only enzyme which oxidizes reduced folates to dihydrofolate, which is then converted back to tetrahydrofolate by another enzyme, dihydrofolate reductase. In general, the limiting intracellular factors in this biochemical pathway for making thymine are, in order of increasing scarcity, deoxyuridylate, dihydrofolate reductase, TS, and then $CH_2FH_4$. Thus, a decrease in thymidine production through the TS pathway can result from nutritional deficiencies which decrease $CH_2FH_4$ production (i.e., primary folate deficiency, B12, B6, and other B-vitamin deficiencies which impair folate one-carbon metabolism), or from antimetabolites drugs such as 5-FU or methotrexate. Methotrexate inhibits dihydrofolate reductase, thus blocking the regeneration of tetrahydrofolates from dihydrofolate. 5-FU and other fluorinated pyrimidines (for example, floxuridine, FUDR or trifluoromethylthymidine) block TS activity through formation of the specific metabolite for this effect, fluorodeoxyuridylate (FdUMP), discussed below.

Inhibition of TS activity leads to "thymineless cell death" or "unbalanced cell growth," whereby RNA and protein synthesis, and cell enlargement, occur in the absence of adequate new DNA synthesis (see Goulian et al., *Adv. Exp. Med. Biol.* 195:89–95 (1986), and refs. therein). In blood cells, such unbalanced cell growth can lead to megaloblastic anemia, macrocytosis, and bone marrow failure.

The mechanism of inhibition of TS by FdUMP has been studied intensively for the past two decades (see Santi et al., *Biochem.*, pp. 8606–13, (1987) and refs. therein). In the absence of $CH_2FH_4$, FdUMP binds TS extremely weakly. However, in the presence of a large excess of $CH_2FH_4$, even low levels of FdUMP will bind tightly to TS, by forming inhibitory TS-FdUMP-$CH_2FH_4$ ternary complexes. In the presence of excess $CH_2FH_4$, such ternary complexes are stable and no significant TS activity occurs. The molecular basis for the ternary complex is that after $CH_2FH_4$ ring-opening to form a covalent bond to FdUMP in the TS enzyme pocket (analogous to the normal reaction with deoxyuridylate), no hydride ion transfer can occur. Thus, no dihydrofolate is formed and the covalently-bonded FdUMP-$CH_2FH_4$ only leaves the enzyme site with great difficulty, as long as free $CH_2FH_4$ is present in substantial excess. If the $CH_2FH_4$ concentration is relatively low, the ternary complex dissociates back to starting products, including free, active TS.

Thus, TS inhibition can occur with only trace amounts of FdUMP in slight excess over TS molecules; however, a specific condition must occur in that 5-10-methylenetetrahydrofolate ($CH_2FH_4$) or tetrahydrofolate ($FH_4$) (and their polyglutamates) must be present in high concentration. Stated more simply, $CH_2FH_4$ is like a "glue" that holds the FdUMP onto the TS enzyme and therefore inhibits TS activity. However, $CH_2FH_4$ is also a powerful growth factor, for promotion of purine, protein, and lipid metabolism, as well as pyrimidine synthesis; thus, $CH_2FH_4$ administration for the purpose of promotion of TS inhibition by FdUMP may be expected to also increase the degree of "unbalanced cell growth."

$CH_2FH_4$ is a normal intracellular metabolite of the B-vitamin, folic acid, for use in thymidylate synthesis by TS. The same is true with respect to the polyglutamates of $CH_2FH_4$. However, $CH_2FH_4$ is also used by several other enzymes including $CH_2FH_4$ reductase (EC 1.1.99.15), serine hydroxymethylase (EC 2.1.2.1), and C1-tetrahydrofolate synthase and $CH_2FH_4$ dehydrogenase (EC 1.5.1.5). These interconversions using $CH_2FH_4$ are essential for purine synthesis, amino acid synthesis (i.e., serine and methionine), and lipid metabolism through the re-methylation of methionine. Thus, $CH_2FH_4$ is located at a metabolic branch point as a substrate for at least 4 different enzymes (Green et al., *Biochem.* 27:8014–22, (1988), S. J. Benkovic, *Ann. Rev. Biochem.* 49:227–51 (1980) and Schirch et al., *Arch. Biochem. Biophys.* 269:317–80 (1989)). This explains the fact that intracellular $CH_2FH_4$ is normally present in low concentrations, below 1.0 micromolar. Recent measurements have shown that intracellular $CH_2FH_4$ levels are typically low, and virtually always lower than tetrahydrofolate, using the bacterial *L. Casei* TS-[3H]FdUMP ligand binding assay (Priest et al., *Cancer Res.* 48:3398–3404 (1988), and refs. therein). The present inventors have modified this assay (*Adv. Exp. Med. Biol.* 244:98–104 (1988) and *Invest. New Drugs* 7:27–36 (1989)) and reported relatively low levels of $CH_2FH_4$ (much below 1.0 micromolar) in patients' cancer biopsy specimens despite administration of high doses of leucovorin (LV) (*Proc. Am. Soc. Clin. Oncol.* 8:69 (1989)). Furthermore, these observations of the present inventors led to administration of the amino acid, L-serine, to patients in an attempt to convert the tetrahydrofolates (in various polyglutamate forms, present in large excess) to $CH_2FH_4$ (and polyglutamates). These results have suggested that increased $FH_4$, rather than $CH_2FH_4$, may be therapeutic. The inventors have recently published the only comparative data that exist for the different major intracellular one-carbon forms of folates (*Biochem. Pharmacol.* 38:2985–93 (1989)), showing that of all of these, $CH_2FH_4$ (at least, as the monoglutamate) is the best folate form for formation of TS-FdUMP-folate ternary complexes, and that a concentration of $CH_2FH_4$ in excess of 1.0 micromolar is desirable for this effect. $CH_2FH_4$ was found to be four times stronger than the next best folate, tetrahydrofolate, and about 100 times stronger than LV. However, to maintain $CH_2FH_4$ as this form (vs. aqueous dissociation to $FH_4$), formaldeyde was required to be present in great excess over the folate at these micromolar concentrations of folate.

Leucovorin (referred to as LV, or folinic acid) is (6R,S)-5-formyl-tetrahydrofolate and has been available commercially for decades for the treatment of folic acid (the B-vitamin) deficiency states (*The Pharmacologic Basis of Therapeutics*, 4th ed. (Goodman et al., eds.) The MacMillan Co., Toronto, pp. 1431–44 (1970)). In 1982, the first clinical reports of the usefulness of LV as a modulator of 5-FU in cancer treatment appeared. (Machover et al., *Cancer Treat. Rep.* 66:1803–07 (1982)). LV addition to 5-FU appeared to approximately double response rates in patients with gastrointestinal cancers. This result was confirmed in several subsequent studies. (For an extensive review, see Grem et al., *Cancer Treat. Rep.* 71:1249–64 (1987)). Currently, LV addition to 5-FU therapy is community standard practice in the United States.

The mechanism of leucovorin (LV or folinic acid) improvement in the antitumor therapy of 5-FU and floxuridine (FUDR) has been shown in several studies to be due to improved TS inhibition associated with increased intracellular (6R)-$CH_2FH_4$ and (6S)-tetrahydrofolates. However, LV appears to be only partially effective in the goal of promoting complete TS inhibition by FdUMP in vivo. For an in vitro example, researchers have shown that TS inhibition after 5-FU, while improved by LV, was still clearly incomplete (Keyomarsi et al., *J. Biol. Chem.* 263:14402–09 (1988)). In part, this may have been related to saturation of obtainable summed pools of $CH_2FH_4+FH_4$ at about a 5-fold increase over baseline at 30 hr LV exposure. Thus, maximum synergy of LV was obtained at less than 1.0 micromolar exposure, with no further improvement at higher concentrations although human plasma folates (LV and methyltetrahydrofolate, MTHF) are higher than this after high-dose LV administration (Doroshow et al., *NCI Monogr*, 5:171–74 (1987)). A related observation may be that addition of high-dose folic acid (140 mg/m²) to 5-FU therapy appears to be associated with an increase in toxicity without improved response rates (Asbury et al, *Am. J. Clin. Oncol.* 10:47–49 (1987)).

In fact, decreasing synergy has been shown for LV addition to FUDR at concentrations above 0.5 micromolar, when the colon cancer cells were previously folate-deficient (Davis et al., *Mol. Pharmacol.* 35:422–27 (1989)). Also, others have shown in vivo in mice that expansion of breast tumor $CH_2FH_4$ pools was a maximum of less than two-fold over baseline despite massive LV dosing (180 mg/kg×8 over 48 hr) (Wright et al., *Cancer Res.* 49:2592–96 (1989)). These observations are mirrored in recent clinical trials comparing the therapeutic outcome in colon cancer, in which low-dose LV (20 mg per square meter) was more effective than high-dose LV (200 mg per square meter) in terms of both tumor response rate and patient survival (Poon et al., *J. Clin. Oncol.* 7:1407–18 (1989)). The lack of effectiveness of high-dose LV in promoting complete TS inhibition was suggested by researchers based on tumor biopsy analyses in breast cancer patients: LV increased TS inhibition from an average of 30±13 to 71±14%, with responding patients showing the higher percentages of TS inhibition than non-responders (Swain et al., (*J. Clin. Oncol.* 7:890–99 (1989)).

In view of the above, the present inventors realized the potential of the direct administration of $CH_2FH_4$ to patients receiving 5-FU, as such a course of action would maximize TS inhibition.

The desirability and ability to use $CH_2FH_4$ in the method of the present invention have never been obvious for various reasons.

For example, $CH_2FH_4$ as a compound in solution has enjoyed a general reputation of being extremely unstable. (Temple et al., "Chemical and Physical Properties of Folic Acid and Reduced Derivatives," In *Folates and Pterins* (Blakely et al., eds.), Vol. 1, pp. 61–63 (1984) and Wright et al., *Cancer Res.* 49:2592–96 (1989)). In solution, it is generally known to exist in equilibrium with $FH_4$, requiring excess formaldehyde ($CH_2O$) to favor the equilibrium toward $CH_2FH_4$.

Under anaerobic conditions, such as made possible for clinical administration of $CH_2FH_4$ or $FH_4$ by a closed, delivery system (U.S. Pat. No. 4,564,054), powdered $FH_4$ is stable even at room temperature, for a year or more (Caldwell et al., *Prep. Biochem.* 3:323-26 (1973)).

Additionally, published data on the clinical tissue levels of $CH_2FH_4$ and $FH_4$ in patients have been limited, and it is well known that LV can be given in gram-size doses (Grem, et al., supra.). LV is an extremely powerful folate (B-vitamin) that is one-hundred times stronger than folic acid in correcting nutritional folate deficiency. As little as 1.0 mg of LV will correct folate deficiency as a single dose (*The Pharmacological Basis of Therapeutics*, supra.). Thus, it is logical to assume that tumor $CH_2FH_4$ and $FH_4$ levels might reach saturation levels from high dose LV.

Finally, it appears that no published studies exist on the toxicological aspects of $CH_2FH_4$ or $FH_4$. More specifically, there seems to be no available published work on either in vitro or in vivo effects of direct exposure of living cells to $CH_2FH_4$ or $FH_4$ except to rescue methotrexate toxicity (Kisliuk et al., *Cancer Treat. Rep.* 61:647-50 (1977)).

Thus, in view of the structural properties of $CH_2FH_4$ and $FH_4$ as well as the lack of information regarding the biological effects of $CH_2FH_4$ and $FH_4$, the present invention is quite remarkable. $CH_2FH_4$ is utilized to potentiate or modulate the antitumor effects of the chemotherapeutic agent 5-FU.

L. R. Hughes (Eur. Pat. Appl. EP 284,3380 and Chem. Abstr. 110:95789 (1989)) has described a novel folate analog as a TS inhibitor and antitumor agent. However, the discovery is clearly radically different from the present invention. The analog does not occur naturally, is absent two nitrogen atoms, is not reduced, and has a reactive propargyl group attached to the glutamate moiety. Also, no mention is made of 5-FU.

Interleukin-2 has been proposed as a modulator of tetrahydrobiopterin (U.S. Pat. No. 4,752,573); however, interleukin-2 is an oligopeptide having no resemblance to leucovorin, and no claim for TS inhibition or interaction with 5-FU is made.

A patent for radiolabeled assay of folates (U.S. Pat. No. 4,136,159) has no therapeutic pharmaceutical intent, and makes no mention of TS inhibition.

Various patents exist for other, unnatural folate analogs, including quinazolines and dideazatetrahydrofolates as inhibitors of enzymes such as folylpolyglutamyl synthetase (e.g., see Chem. Abstr. 110: P39366p (1989)). However, these are unnatural analogs which have distinct chemical, structural differences from $CH_2FH_4$.

The European patent application (EP 266,042) of Wood et al. describes a process for separation of diastereomers of LV, as well as (6R)- and (6S)-tetrahydrofolates. No use of $CH_2FH_4$ or $FH_4$ as a potentiator of TS inhibition by FdUMP (and thus 5-FU and other fluoropyrimidines) is claimed in the document.

All U.S. patents and publications referred to herein are hereby incorporated by reference.

SUMMARY OF THE INVENTION

The present invention relates to the compound $CH_2FH_4$ and its solution product isomer $FH_4$, therapeutic uses of these compounds, and compositions thereof. $CH_2FH_4$ and $FH_4$ strongly potentiate the antitumor or TS-inhibitory effects of 5-FU.

More specifically, the present invention includes a method of inhibiting the growth of a tumor in a patient comprising administering to said patient an amount of parent $CH_2FH_4$ or $FH_4$ and 5-FU sufficient to effect said growth inhibition. The $CH_2FH_4$ or $FH_4$ may be administered concurrently with 5-FU, or prior to the administration of 5-FU. In the latter case, the $CH_2FH_4$ or $FH_4$ is administered 6-24 hours, or preferably 1-3 hours, before the administration of the 5-FU.

The $CH_2FH_4$ or $FH_4$ may also be administered after the administration of 5-FU in which case the $CH_2FH_4$ or $FH_4$ compound is administered 1-10 days, or preferably 1-6 hours, after the 5-FU administration.

Furthermore, the $CH_2FH_4$ or $FH_4$ solution may be administered either intravenously, intraarterially, or intraperitoneally, and in a dosage of 5-500 mg/m$^2$ (body surface area). Preferably, it may be administered in a dosage of 20-200 mg/m$^2$ (body surface area). The $CH_2FH_4$ or $FH_4$ solution may also be administered orally or topically as a 0.5% cream under an occlusive dressing.

If it is administered intravenously, such as through a central venous catheter, the $CH_2FH_4$ or $FH_4$ solution may be given in a dosage of 5-500 mg/m$^2$ (body surface area), or preferably 20-200 mg/m$^2$, every 4-6 hours, once daily, or once weekly or as a continuous infusion of 20-200 mg/m$^2$/week. Additionally, if it is administered every 4-6 hours, the $CH_2FH_4$ or $FH_4$ solution may be administered prior to, or subsequent to, the administration of 5-FU.

The $CH_2FH_4$ or $FH_4$ may be administered as the 6R, 6S, or as a mixture of the 6R and 6S enantiomers (diastereomers). Furthermore, one may vary when to administer the compounds. For example, the natural (6S) diastereomer of $FH_4$ may administered 6-24 hours before administration of 5-FU, or the natural (6S) diastereomer of $FH_4$ may administered 1-6 hours after administration of 5-FU. The natural (6S) diastereomer of $FH_4$ may be administered concurrently with 5-FU. Similarly, the unnatural (6R) diastereomer of $FH_4$ may be administered 1-6 hours after the administration of 5-FU, or the unnatural (6R) diastereomer of $FH_4$ may be administered 6-24 hours after the administration of the natural isomer if the natural isomer is administered after the 5-FU.

Also, if the $CH_2FH_4$ or $FH_4$, is administered in an alkaline vehicle, the concentration of the $CH_2FH_4$ or $FH_4$ is from 0.1 to 20 mg/ml whereas if the compound is administered in physiologic saline, the concentration is from 0.1 to 10 mg/ml.

Furthermore, the present invention includes a method of using $CH_2FH_4$ or $FH_4$ in order reduce the toxicity of an anti-folate drug which has been administered to a patient. Examples of anti-folate drugs include methotrexate, trimetrexate, nitrous oxide, and dideoxytetrahydrofolic acid.

The present invention also includes a method of treating folate deficiency states by the administration of $CH_2FH_4$ or $FH_4$.

Moreover, the present invention also includes a method of treating B12- and B6- refractory anemias whereby $CH_2FH_4$ or $FH_4$ is administered in an amount sufficient to effect said treatment.

Furthermore, the present invention also includes a composition containing $CH_2FH_4$ or $FH_4$ and 5-FU, as well as a pharmaceutically active carrier. The composition may also contain a stabilizing agent such as an ascorbate salt, or glutathione. The composition may also contain free formaldehyde. The $FH_4$ may be present in its natural (6S) diastereomeric form or in its unnatural (6R) diastereomeric form.

Additionally, the present invention also includes a composition containing $CH_2FH_4$ or $FH_4$ and a compound which is metabolized to FdUMP, as well as a pharmaceutically active carrier. Examples of compounds which can be metabolized to FdUMP include floxuridine (FUDR), ftorafur (tegafur), and 5'-deoxyfluorouridine (Doxifluridine ®). The composition may also contain a stabilizing agent, such as an ascorbate salt, or glutathione. Formaldehyde may also be present in the composition.

The present invention also encompasses a method of inhibiting the growth of a tumor in a patient, and inhibiting TS activity in the tumor, comprising administering to the patient an amount of unnatural diastereomer (6S)-$CH_2FH_4$ or unnatural diastereomer (6R)-$FH_4$ sufficient to effect the growth and activity inhibition. The unnatural diastereomer (6S)-$CH_2FH_4$ or unnatural diastereomer (6R)-$FH_4$ is administered in a dosage of 5-500 mg/m$^2$, and preferably, in a dosage of 20-200 mg/m$^2$.

The natural diastereomer may be administered with the unnatural diastereomer. For example, the natural diastereomer (6S)-$FH_4$ and the unnatural diastereomer (6R)-$FH_4$ may be administered together in a ratio of from 1:20 to 20:1. The sum of the diastereomers is 5-500 mg.

The invention also includes a composition comprising (6R)-$FH_4$ and a pharmaceutically acceptable carrier and a composition comprising (6S)-$CH_2FH_4$ and a pharmaceutically acceptable carrier.

DETAILED DESCRIPTION OF THE INVENTION

One embodiment of the present invention relates to the use of $CH_2FH_4$ as a modulator of 5-FU in cancer chemotherapy. $CH_2FH_4$ as well as $FH_4$, increase response rates to 5-FU as a result of increasing the inhibition of TS by the 5-FU metabolite, FdUMP, in tumors. Thus, $CH_2FH_4$ can be used to inhibit the growth of tumors when used in combination with 5-FU, or with other drugs which are metabolized to FdUMP including floxuridine (FUDR), ftorafur (tegafur), and Doxifluridine ® (5'-deoxyfluorouridine).

The mechanism of action of $CH_2FH_4$ is promotion of TS inhibition by FdUMP in fluoropyrimidine-treated tumors, which can occur by increasing the rate of formation and stability of TS-FdUMP-$CH_2FH_4$ and TS-FdUMP $FH_4$ ternary complexes. The TS-FdUMP-$FH_4$ complexes are probably the therapeutic objective for both the natural ((6S)-$FH_4$) and unnatural ((6R)-$FH_4$) forms versus complexes with $CH_2FH_4$. The blood and tumor tissue levels of $FH_4$ are much higher than $CH_2FH_4$. (6S)-$FH_4$ (especially polyglutamates) can form very strong ternary complexes without a risk of "fueling" residual TS activity as can occur with $CH_2FH_4$, and at the same time promote unbalanced growth. Furthermore, the unnatural (6R)-$FH_4$ forms stronger (inhibitory) ternary complexes in the absence of excess formaldehyde. Administration of $CH_2FH_4$ (as parent powder) in doses ranging from 5-500 mg/m$^2$ (body surface area), or preferably 20-200 mg/m$^2$, will result in expansion of intracellular pools of $FH_4$ as monoglutamates. One carbon exchange between endogenous $CH_2FH_4$-polyglutamates and tetrahydrofolatemonoglutamate resulting from $CH_2FH_4$ administration, as suggested in Tables II and III, would indicate that the optimal times for bolus 5-FU administration are concurrently or at several hours after bolus I.V. $CH_2FH_4$ administration and thus after maximum polyglutamation. $CH_2FH_4$ may also be administered after 5-FU is given or as a protracted, continuous infusion.

More specifically, $CH_2FH_4$ may be administered 6-24 hours, or preferably, 1-3 hours, prior to the administration of 5-FU. $CH_2FH_4$ can also be administered 1-10 days, or preferably 1-6 hours, subsequent to the administration of 5-FU.

Figure 1:
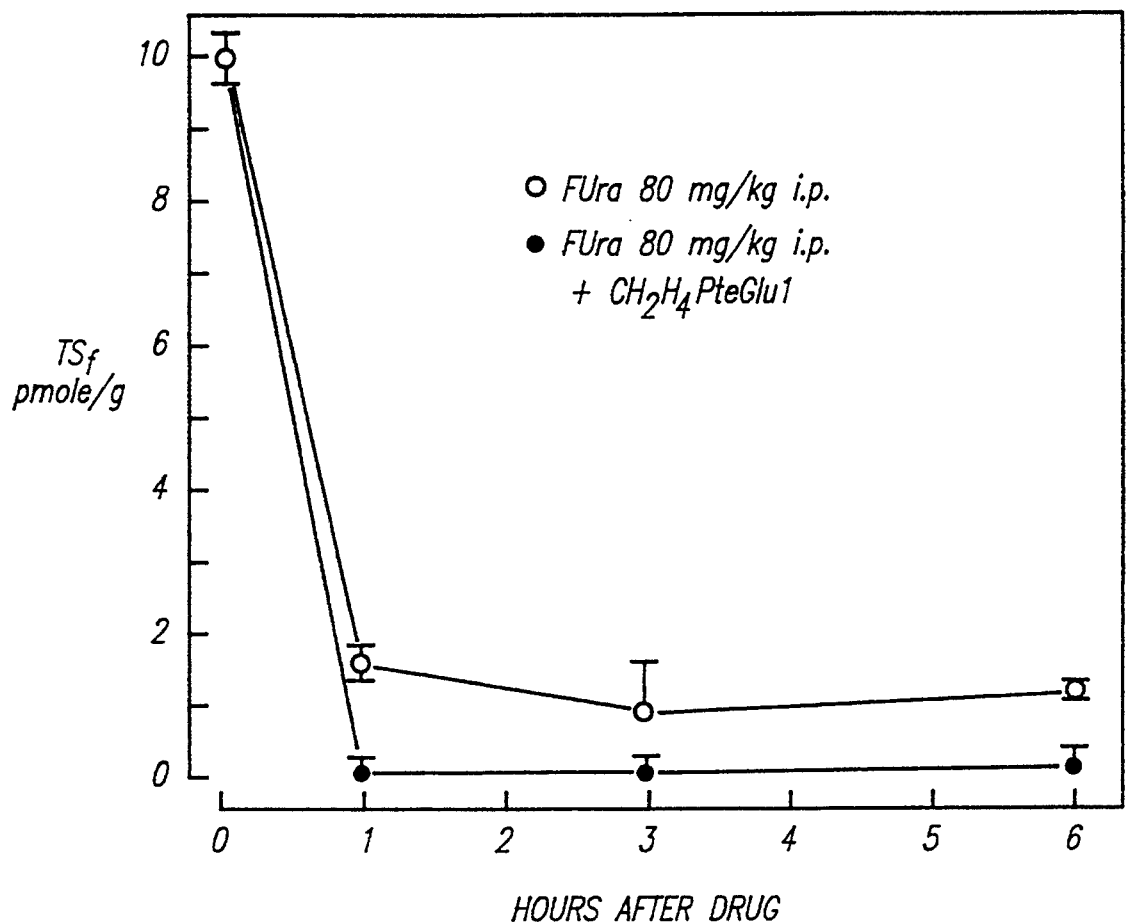
FIG. 1 represents the effect of $CH_2FH_4$ ("$CH_2H_4Pte$-$Glu_1$") on TS inhibition in 5-FU-resistant colon cancer cells (from tumor 51) after the administration of 5-FU ("FUra").
Figure 2:
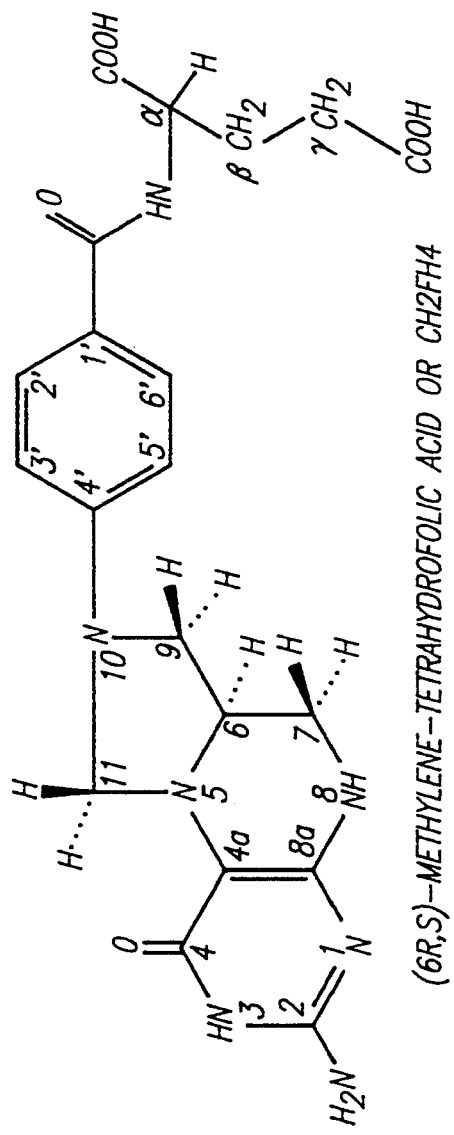
FIG. 2 represents the structure of (6R,S)-methylenetetrahydrofolic acid (or $CH_2FH_4$) and the configuration of the natural (6R)-$CH_2FH_4$ enantiomer (diastereomer) (Poe et al., *Biochem.* 18:5528 (1979) and Kalbermatten et al., *Helv. Chim. Acta* 64:2633 (1981)).
Figure 2:
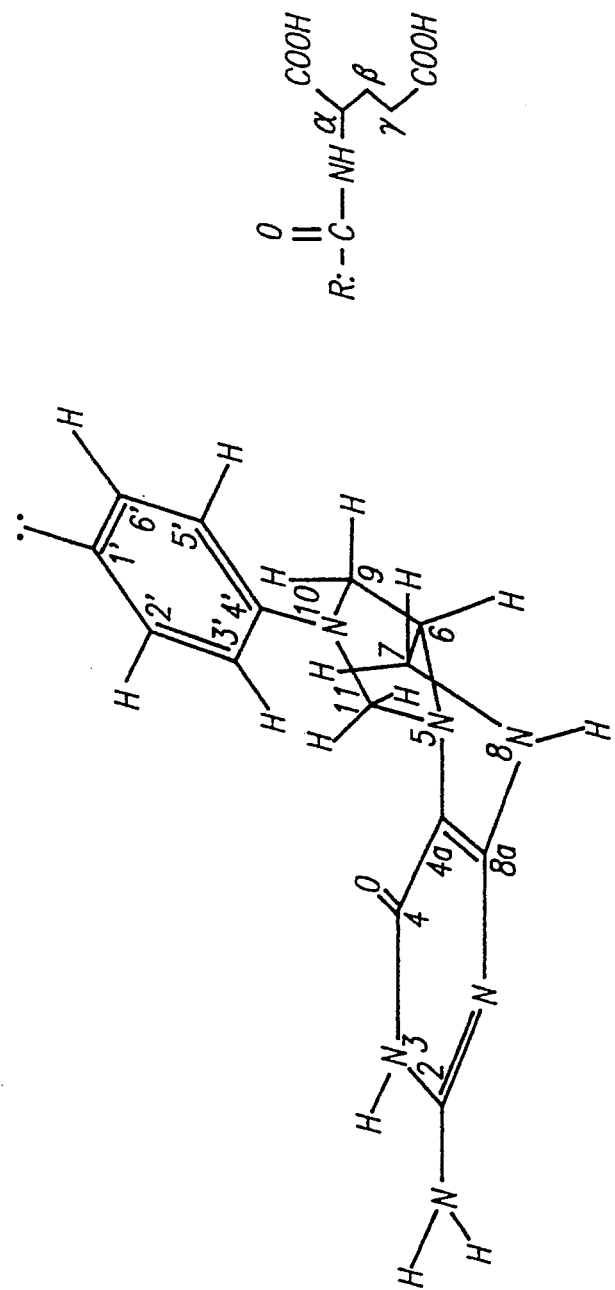

Polyglutamation of folates causes retention within the cell, and typically also accelerates rates of enzyme processing of one-carbon interconversions of folates (Schirch et al., *Arch. Biochem. Biophys.* 269:371-80 (1989), Green et al., *Biochem.* 27:8014-22, 1988). Current data would suggest that polyglutamation of $FH_4$ and $CH_2FH_4$ will promote TS-FdUMP-folate inhibitory ternary complex formation to a greater extent than promotion of the normal enzymic reaction with deoxyuridylate (Houghton et al., *Cancer Res.* 48:3062-69 (1988)). Since polyglutamates may form TS-FdUMP-folate ternary complexes as much as 50-fold more tightly than parent monoglutamates, an objective of folate addition to fluoropyrimidine therapy could also include formation of TS-FdUMP-tetrahydrofolates, which would also be strongly inhibitory. In addition, a role for the unnatural enantiomers (diastereomers at the pterin C6- position), such as polyglutamates of (6S)-$CH_2FH_4$ or (6R)-$FH_4$, in TS inhibition by forming TS-deoxyuridylate-folate or TS-FdUMP-folate ternary complexes, potentially could be a factor (Kisliuk et al., *Biochem.* 20:929-34 (1981)) in the TS inhibition observed with $CH_2FH_4$ administration in vivo (Tables I, II, and III; FIG. 1).

The potentiation of TS inhibition by low levels of FdUMP may be expected to last only a few hours unless polyglutamation of the $CH_2FH_4$ and $FH_4$ occurs thereby creating more powerful TS-FdUMP binders than the parent monoglutamate. Thus, $CH_2FH_4$ dosing requirements may be as frequent as every 4-6 hrs., once daily, or as infrequent as once weekly.

In one embodiment of the present invention, $CH_2FH_4$ can be administered by intermittent (e.g., daily) bolus dosing in patients who have central venous catheters. Such patients could self-administer the $CH_2FH_4$ (using a means for ensuring the stability of the formulation to oxidation) and would also be candidates for administration of $CH_2FH_4$ by continuous, intravenous protracted infusion. The 5-FU infusion would be expected to produce low levels of FdUMP in tumors. Low FdUMP levels would be expected to be associated with relatively poor TS inhibition unless $CH_2FH_4$ levels were very high. $FH_4$, free of formaldehyde as a stabilizer may also be administered in the same manner.

An ameliorating factor to consider may be that chronic TS inhibition, albeit incomplete, would be expected to cause slight increases in $CH_2FH_4$ levels because of lowered consumption of $CH_2FH_4$ in the natural TS mechanism so that pharmaceutical $CH_2FH_4$ in this setting might be more efficient.

Other embodiments include the addition of $CH_2FH_4$ at late times after bolus intravenous 5-FU infusion (e.g., at 6 hours in the daily 25 (monthly) Schedule, or at days 4, 5 and 6 on the biweekly bolus schedule.)

In addition to being administered intravenously, $CH_2FH_4$ may also be administered intraarterially or intraperitoneally, also in a dosage of 5–500 mg/m$^2$, or preferably, in a dosage of 20–200 mg/m$^2$. However, $CH_2FH_4$ may also be administered topically as a 0.5% cream under an occlusive dressing.

Another embodiment of the present invention comprises a composition containing $CH_2FH_4$ (or $FH_4$ in solution) as well as 5-FU. The composition also contains a pharmaceutically active carrier, and may also contain formaldehyde in excess as a stabilizer against oxidation.

A further embodiment of the present invention includes a composition containing $CH_2FH_4$ and one or more other drugs which can be metabolized to FdUMP. The composition may contain a pharmaceutically active carrier, and may also contain formaldehyde in excess as a stabilizer.

It should be noted that $FH_4$, free of formaldehyde, can replace the use of $CH_2FH_4$ in each of the above embodiments. Each of the two compounds has a natural and unnatural diastereomeric form (i.e., natural (6R)-$CH_2FH_4$, unnatural (6S)-$CH_2FH_4$, natural (6S)-$FH_4$ and unnatural (6R)-$FH_4$). Each form may be administered before, after, or concurrently with 5-FU. Furthermore, the unnatural forms may be used alone in a dosage of 5–500 mg/m$^2$, without fluoropyrimidines, as agents for TS inhibition and inhibition of tumor growth. Moreover, different ratios of (6S)-$FH_4$ and (6R)-$FH_4$ together may be utilized in treatment if provided in a 1:20 to 20:1 ratio (5–500 mg/m$^2$ sum).

It should also be noted that the different diastereomers may be given at different times to the same patient. For example, the natural (6S)-$FH_4$ (solution of (6R)-$CH_2FH_4$) may be administered several minutes or hours before or after (or concurrently with) 5-FU administration. The unnatural (6R)-$FH_4$ (solution of (6S)-$CH_2FH_4$ powder) may then be administered several hours later, at a time when the cancer cells are recovering from unbalanced growth and new TS activity is occurring.

Because reduced folates are rapidly interconvertible according to their one-carbon states, it may be anticipated that the clinical tolerance for $CH_2FH_4$ or $FH_4$ will be similar to that of LV (6R,S-leucovorin) and 5-methyl-(6R, S)-tetrahydrofolate (MTHF), the natural diastereomer of the latter being the predominant blood transport form of folates.

Also, $FH_4$, and possibly $CH_2FH_4$, have recently been reported as accumulating to low but significant (i.e., less than 20 micromolar) concentrations in human plasma after LV administration to human subjects (Bunni et al., Cancer Chemother. Pharmacol. 23:353-57 (1989)).

Thus, it can be anticipated that the dose tolerance for $CH_2FH_4$ or $FH_4$ in humans is similar to the reported experiences with LV and methyltetrahydrofolate (MTHF) (both of which are given as a mixtures of enantiomers (diastereomers)). Specifically, an upper limit of 500 mg per square meter body surface area would be expected to be therapeutically effective. The lowest effective dose may possibly be more powerful than either LV or MTHF, and thus could be as low as 5 mg per square meter body surface area in a single dose. A dosage of 20–200 mg/m$^2$ (body surface area) is preferred.

Based on previous studies of the toxicology of folates (LV, MTHF and folic acid) combined with 5-FU and fluorodeoxyuridine, the LD50 in rats would be expected to be above 150 mg/kg i.v. (single bolus) with regard to $CH_2FH_4$ or $FH_4$, and may be expected to cause convulsions in such high doses (Bartosek et al., Chemioterapia Oncologica 2(4): 85-98 (Dec. Supp, 1987)).

The pH of the $CH_2FH_4/FH_4$ solution which is to be injected, may range from slightly acidic to slightly alkaline. 5-FU up to 50 mg/mL in alkaline media may be present, analogous to the practice of formulation of 5-FU and LV in the same solution (e.g., Trave et al., J. Clin. Oncol. 6:1184-91 (1988)). Furthermore, the concentration for injection may be as high as 100 mg/10 mL, preferably from 0.1 to 20 mg/ml, in alkaline vehicles. The concentration may also be as high as 100 mg/20 mL, preferably from 0.1 to 10 mg/ml, in physiologic, normal saline. At concentrations less than 1 mM in initial $CH_2FH_4$ concentrations, the predominant form in solution is $FH_4$ (i.e., the dilution of $CH_2FH_4$ in aqueous solution shifts the equilibrium between $FH_4$ and $CH_2FH_4$ towards $FH_4$, regardless of pH, $O_2$ tension, or the presence of reducing agents).

Ascorbate salts may be present as stabilizers (e.g., 1% w/v as the salt at neutral or slightly alkaline pH). Other reducing substances may also be used as stabilizers, for example, reduced glutathione.

Free formaldehyde ($CH_2O$) may also be present in concentrations up to 10 mM. However, the dosage must be adjusted for formaldehyde toxicity. The formulation may be made directly from (6R,S)-$FH_4$ powder, alternatively. In this case, formulations would be checked and controlled for the degree of spontaneous condensation of formaldehyde as a contaminant from ambient air to form $CH_2FH_4$ (Pogolotti et al., Biochem. 18:2794–2804 (1979)). The oral LDLo (or lowest lethal dose) of $CH_2O$ in humans has been reported to be 36 mg/kg (Registry of Toxic Effects of Chemical Substances, US DHHS, PHS, CDC, NIOSH, Vol. 1, p. 822 (1980)). The pure (6R)$CH_2FH_4$ or (6S)$FH_4$ enantiomer may also be utilized, free of the unnatural (6S)$CH_2FH_4$ or (6R)$FH_4$ enantiomer, respectively. Enantiomer (diastereomer) separation is obtainable by chiral column or DEAE column preparative isolation (Kaufman et al., J. Biol. Chem. 238:1498–1500 (1963)).

A possible major advantage of $CH_2FH_4$ over $FH_4$ as the parent powdered material is the protection against air oxidation, referred to above, which protection would therefore be greater with concentrated versus dilute (e.g., <0.5 mM) concentration, in the absence of a mechanism for excluding air during reconstitution and administration (as provided by the Protector device).

It appears that direct administration of $CH_2FH_4$ or $FH_4$, either as the mixture of 6R and 6S diastereomers (enantiomers), the unnatural $6S-CH_2FH_4$, or the natural $6R-CH_2FH_4$ alone (or their $FH_4$ solution equilibrium products, referred to as solution product isomers (see pages 1 and 10)) can overcome some of the disadvantages of LV described above. That is, $CH_2FH_4$ addition to 5-FU can lead to greater tetrahydrofolate ($FH_4$) and $CH_2FH_4$ elevations intracellularly than LV or MTHF (which both require one carbon activation), and consequently show more profound synergism on TS inhibition by FdUMP.

The applications for $CH_2FH_4$ or $FH_4$ are quite significant and far-reaching. For example, antitumor uses of $CH_2FH_4$ or $FH_4$, combined with TS-inhibitory fluoropyrimidines include: 1) addition to Platinol/5-FU infusion therapy in head and neck cancer and other epidermoid cancers, 2) addition to combination cyclophosphamide/doxorubicin/5-FU in breast cancer 3) addition to topical Efudex® (5-FU) cream under an air-free occlusive dressing for skin conditions (for example benign keratoses, keratoacanthomas, verrucae, premalignant keratoses, in situ cancer and invasive superficial malignancies amenable to topical therapy). Furthermore, $CH_2FH_4$ or $FH_4$ can also be applied to those cancer types in which 5-FU and floxuridine are typically combined with LV, such as in colon, rectal and pancreatic carcinomas.

$CH_2FH_4$ or $FH_4$ can also be utilized with respect to non-malignancy related conditions. For example, the natural diastereomers of $CH_2FH_4$ or $FH_4$ can be used with respect to B12- and B6-refractory anemias which are not responsive to LV. $CH_2FH_4$ or $FH_4$ can also be used to treat folate deficiencies. Furthermore, $CH_2FH_4$ and $FH_4$ can also be used for the potentiation (selective rescue of the host patient) of the TS inhibitory mechanism of antibacterial action of nucleotide analogs.

Additionally, $CH_2FH_4$ or $FH_4$ can be utilized to reduce the toxicity of anti-folate drugs which have been administered to patients. Such anti-folate drugs include, for example, methotrexate, trimetrexate, nitrous oxide, and dideoxytetrahydrofolic acid.

As a rescue agent following methotrexate, $CH_2FH_4$ or $FH_4$ may be more specific than the presently used LV (or MTHF) since $CH_2FH_4$ would require less (or no) metabolic activation in the case of $FH_4$ to provide for purine, pyrimidine, and the amino acid synthetic requirements normally met by intracellular folates. $CH_2FH_4$ could also therefore become useful in rescue of the host in the trimetrexate treatment of *Pneumocystis carinii* infections of immunosuppressed patients (i.e., AIDS patients).

The present invention can be illustrated by the use of the following non-limiting examples.

EXAMPLE 1

Synthesis of $CH_2FH_4$ as a Low-Formaldehyde Material

Preparation of $(6R,S)-CH_2FH_4$ $CH_2FH_4$ as the equal mixture of diastereomers (optical isomers or enantiomers at the C6-position; both diastereomers are of the natural L-configuration at the alpha-carbon position of the glutamate moiety) was prepared from $(6R,S)$-tetrahydrofolic acid, commercially available from Sigma, in the examples described below. The method of synthesis has been described previously (C. P. Spears and B. Gustavsson, *Adv. Exp. Med. Biol.* 244:98-104 (1988)). To (6R, S)-tetrahydrofolate (6R, $S-FH_4$) powder, (100 mg) is added 360 µL of 1.0M Na Ascorbate, pH 6.5, 68 µL of 37% (w/w) formaldehyde ($CH_2O$), and 16 mL phosphate buffer, pH 7.0. A 10-min room temperature incubation allows completion of formation of $(6R,S)-CH_2FH_4$. This material is applied to a DEAE-cellulose column using a modification of a well-known procedure (Kaufman et al., *J. Biol. Chem.* 238:1498-1500 (1963)). A step elution with $NH_4HCO_3$ buffers of increasing concentration and pH, leads to isolation of $CH_2FH_4$ in the last pooled fraction. This material does not contain free formaldehyde as assayed colorimetrically, or by toluene extraction of dimedone (methone)-trapped [11-$^{14}$C] $CH_2FH_4$, prepared with [$^{14}$C]$CH_2O$ as described previously (Moran et al. Proc. Natl. Acad. Sci. USA 76:1456-60, 1979). Phosphate buffers and TEAE-cellulose can also be used in the procedure of Kaufman, which gives both enantiomers of $CH_2FH_4$ in the same peak; however, if potassium bicarbonate buffer is used, a separation of the enantiomers is effected, with the biologically active, natural-configuration, $(6R)-CH_2FH_4$ peak eluting after the $(6S)-CH_2FH_4$ peak. The amount of formaldehyde (as methylene) in the product may, in fact, be even less than stoichiometric with tetrahydrofolate ($FH_4$) (Horwitz et al, *J. Med. Chem.* 12:49-51 (1969)). The amount of $(6R)-CH_2FH_4$ in the preparations is checked by one or more of the three following methods. (1) Spectrophotometrically, by use of this material as the limiting substrate in a TS assay with *L. Casei* enzyme, as described by Daron et al. (*J. Biol. Chem.* 253:940-45 (1978); (2) ligand binding assay using [6-3H]FdUMP and *L. Casei* TS described by the inventors (*Adv. Exp. Med. Biol.* 244:98-104, 1988); and by absorbance at 294 nm on HPLC (Lu et al., Biochem. 23:6870-75 (1984)). Column-isolated $CH_2FH_4$, whether racemic in 6R- and 6S-forms or as the 6R-form alone in solution can be stored under argon at $-80°$ C. for up to a year without decomposition (Bruice, et al. *Biochem.* 21: 6703-09 (1982)). Alternatively, solutions of $CH_2FH_4$ after column isolation can be lyophilized to powder and stored under nitrogen in sealed glass ampoules. Various ratios of formaldehyde to $CH_2FH_4$ can be used, from less than stoichiometric, as described above, including no formaldehyde (either bound as methylene, or free) to a 2- to 4-fold or more excess (Bruice, et al., *Biochem.* 21:6703-07, (1982)). The use of 2-mercaptoethanol or other reduced thiols has been advocated by some workers, but is unnecessary and may cause minimal interference (S. F. Zakrewski, *J. Biol. Chem.* 241:2957-961 (1966) and Kallen et al. *J. Biol. Chem.* 241:5845-50 (1966)) in condensation of $CH_2O$ with tetrahydrofolate.

Alternative methods for synthesis and purification of $(6R,S)-CH_2FH_4$ are reviewed by C. Temple, Jr. and J. A. Montgomery, In: *Folates and Pterins* (R. L. Blakley and S. J. Benkovic, eds.), vol. 1, Chemistry and Biochemistry of Folates, John Wiley & Sons, New York, pp. 61-120 (1984). This includes use of (6R,S)5-formyltetrahydrofolate (leucovorin or LV), which is commercially available in bulk quantities, and is converted to the 5,10-methenyltetrahydrofolate by acidic conditions. The latter compound then can yield $CH_2FH_4$ by reduction with borohydride in DMSO and pyridine (Farina et al., *J. Am. Chem. Soc.* 95: 5409 (1973)).

Preparation of (6R)-CH$_2$FH$_4$

The naturally-occurring diastereomer (enantiomer) of CH$_2$FH$_4$, (6R)-CH$_2$FH$_4$, can be prepared by a number of methods, including that of Kaufman et al. as described in the foregoing section, using TEAE-cellulose elution by bicarbonate. Commercially-available folic acid reduced to dihydrofolate using hydrosulfite (Mathews et al. *J. Biol. Chem.* 235:3304–08, (1960)) or dithionite (R. L. Blakley, *Nature* 188:231–32, (1960)) is used as a substrate for purified dihydrofolate reductase in the present of NADPH (e.g., see M. Poe et al, *Biochem.* 18:5527–30 (1979)). Formation of (6S)-tetrahydrofolate (which is the natural diastereomer) is readily followed at 294 nm. Purification is then done by chromatography (e.g., S. F. Zakrewski and A. M. Sansone, *Methods Enzymol.* 18B:728–31, 1971), followed by lyophilization to powder and storage under nitrogen or argon in sealed glass vials.

An additional approach is reduction of dihydrofolic acid by dihydrofolate reductase in the presence of formaldehyde (Horne et al., *Methods Enzymol.* 66:545ff (1980)), followed by column isolation, which avoids the need for a separate CH$_2$O step after (6S)-tetrahydrofolate isolation. In these preparations, ascorbate is typically present (e.g., 0.1M) as an antioxidant. Synthesis of the unnatural (6S)-CH$_2$FH$_4$ isomer has been described, by selective enzymic conversion of (6R)-CH$_2$FH$_4$ to dihydrofolate, which is easily separated by column chromatography (*Anal. Biochem.*, Vol. 154, pp 516–24 (1986)). The isomeric solution of (6S)-FH$_4$ is then obtained by dilution to less than 0.5 mM.

Stability of CH$_2$FH$_4$

Solutions of CH$_2$FH$_4$, as well as the powder, are unstable in the presence of oxygen, with oxygen degradation being catalyzed by light, acid, base, and heavy metals (R. G. Kallen, *Methods Enzymol.* 183:705ff, 1971). CH$_2$FH$_4$ is somewhat more stable than FH$_4$, as are the major N5-substituted tetrahydrofolates; FH$_4$ solutions can undergo 90% degradation in 4.1 hr when exposed to air (discussed in C. Temple, Jr., and J. A. Montgomery, supra. However, tetrahydrofolate (FH$_4$) is completely stable under anaerobic conditions Caldwell et al., *Prep. Biochem.* 3:323–26 (1973).

Thus, a method for air-free reconstruction of CH$_2$FH$_4$ or FH$_4$ powder (in vacuum, or under nitrogen or argon in air-tight ampoules), or fresh handling of column-isolated CH$_2$FH$_4$ or FH$_4$, is required to ensure the stability of CH$_2$FH$_4$ as a pharmaceutical with accurate dosing. The invention of Gustavsson, one of the present inventors, (U.S. Pat. No. 4,564,054) referred to as the Protector device, affords such a method. The Protector invention is not generally known, since it is marketed as a method for prevention of aerosolization of mutagenic/toxic cancer chemotherapy agents, however, it is equally useful for air-free reconstitution, dosing, and i.v. administration of drug solutions to patients. The Protector is suitable for handling all anticipated dose ranges and concentrations of CH$_2$FH$_4$, with the volume for dosing limited only by the syringe size. Vehicles for reconstitution of CH$_2$FH$_4$ or FH$_4$ powder include 5% dextrose, normal (0.89% w/v) saline, 5-FU solutions, and sterile water, (which may or may not be de-aerated for removal of dissolved oxygen prior to use in reconstitution of CH$_2$FH$_4$ or FH$_4$ powder, depending on the presence in the formulation of antioxidant stabilizers such as ascorbate). The Protector may be modified to use semi-opaque materials, such as brown plastic, to reduce transmission of ambient light.

EXAMPLE 2

CH$_2$FH$_4$ Use With 5-FU in Murine Colon Carcinoma CA51

(6R, S)-CH$_2$FH$_4$ was prepared by the DEAE-cellulose column procedure, described above, using step-elution of the material as previously reported for purification of nucleotides (Moran et al., *Proc. Natl. Aca. Sci. USA* 76:1456–60 (1979)). To twenty micromoles of (6R,S)-FH$_4$ (Sigma) were added 62.5 ul of 1.0M Na Ascorbate, pH 6.5, 2.7 ul of 37% formaldehyde stock, and 0.6 mL of 5 mM phosphate buffer, pH 7.0. Because of the high formaldehyde, this solution was over 2 mM in CH$_2$FH$_4$, with less FH$_4$ present as the solution isomer. After 20 min at room temperature, this solution was applied to a 1×3-cm DEAE-cellulose column; in the last step, the 500 mM NH4HCO3 (pH 8.0) fraction (30 mL) was pooled, lyophilized to dryness, and stored under vacuum in glass ampoules. This fraction contains both diastereomers of CH$_2$FH$_4$. Spectrophotometric assay (which uses mM concentrations of folate and CH$_2$O) of powder reconstituted in phosphate-buffered-saline showed a concentration of the natural (6R)-CH$_2$FH$_4$ in this solution of 2.4 mM; prior assay by *L. casei* TS-3H]FdUMP-folate ternary complex formation gave a concentration of 2.5 mM.

On the day of reconstituting the above CH$_2$FH$_4$, mice bearing subcutaneous murine colon carcinoma Tumor 51 were administered intraperitoneal (i.p.) 5-FU, with or without concomitant i.p. CH$_2$FH$_4$ by separate injection. The 5-FU was given at a dose of 1.6 mg per mouse, about 80 mg/kg. The CH$_2$FH$_4$ was given at a dose of 0.5 mL of the 2.4 mM material (1.2 mmole/mouse), above. The in vivo methodologies were essentially as had previously been described (C. P. Spears, et al., *Cancer Res.* 42:450–56 (1982)). In contrast, however, to the extensive prior experience of the present inventors with this 5-FU-resistant tumor line, which always had shown significant FdUMP-titratable free TS levels, the tumors of mice receiving concomitant CH$_2$FH$_4$ showed abrogation of TS activity (Table I and FIG. 1). The free TS levels of the 5-FU-only treated mice were comparable to the previous observations of the inventors in this line, and at the 1.0 pmol/g level of TS activity was sufficient to support thymidylate synthesis required for tumor growth (C. P. Spears, *Exerpta. Med. Int. Congr. Series* 647:12–19, (1984)). The levels of apparent free TS in tumors of mice receiving CH$_2$FH$_4$ concomitant with 5-FU were at, or below, that level due to exchange-labeling of endogenous TS-FdUMP-folate ternary complexes in the cytosolic extracts. Stated otherwise, the average ± S. D. apparent TS value of 0.42±0.20 pmol/g for the 5 tumors of the 5-FU+CH$_2$FH$_4$ treatment group when corrected downward for labeling of endogenous FdUMP-inhibited enzyme by a minimum correction factor of 5% (Spears and Gustavsson, *Adv. Exp. Med. Biol.* 244:98–104, (1988)) equates with zero detectable TS activity. This is exactly the qualitative difference between sensitivity and resistance to 5-FU previously established (see Spears et al., *Cancer Res.* 42:450–52 (1982)). An additional observation was that in the Tumor 51 specimens from mice receiving CH$_2$FH$_4$ concomitant with 5-FU was that the pre-incubation dissociation condition, which had previously been routinely used for regenerating all TS in the free form, was completely unable to regenerate free TS, in contrast to the more normal findings in the 5-FU-only exposed tumors. This is strongly suggestive that $CH_2FH_4$ administration raised concentrations of tumor $CH_2FH_4$ and $FH_4$, so high, that even after large dilution into the assays the concentrations were still above those that could spontaneously oxidize to lower levels permitting in vitro ternary complex dissociation.

The results obtained from Example 2 are shown in FIG. 1, and in Table I.

TABLE I

TS INHIBITION IN MURINE TUMOR CA51 AFTER 5-FU[a] EFFECT OF CO-ADMINISTRATION OF $CH_2FH_4$[b]
(Values = Ave. ± S.D.)

| | 5-FU Alone | | 5-FU + $CH_2FH_4$ | |
|---|---|---|---|---|
| Hours | Free TS[c] (pmol/g) | % Inhibition | Free TS[c] (pmol/g) | % Inhibition |
| 1 | 1.67 ±0.28 | 83.3 ±2.8 | 0.41 ±0.26 | 95.9 ±2.6 |
| | | | 0.164 ±0.13 | 98.4 ±1.3 |
| 3 | 1.00 ±0.72 | 90.0 ±7.2 | 0.36 ±0.06 | 96.4 |
| | | | 0.71 ±0.03 | 92.9 |
| 6 | 1.27 ±0.06 | 87.3 ±0.6 | 0.46 ±0.05 | 95.4 |

[a]80 mg/kg i/p.
[b]27 mg/kg in (6R) $CH_2FH_4$ by spectrophometric and binding assays.
[c]Not corrected for ternary complex exchange labeling or ratio of $CH_2FH_4$ to $FH_4$. A minimal correction factor of 5% leads to the calculation that there was 100% TS inhibition for all tumors receiving the combination of 5-FU and $CH_2FH_4$, compared to only 92% average TS inhibition by 5-FU alone. Baseline total TS was 10.00 ± 0.04 pmol/g.

EXAMPLE 3

Effect of $CH_2FH_4$ on Two Patients Who Had Already Received Treatment With 5-FU $CH_2FH_4$ was formulated, assayed, and administered to 2 patients who had previously been treated with 5-FU. The assays were performed by the methods described in Spears et al., Adv. Exp. Med. Biol. 244:98–104 (1988). In the data shown, the TS inhibition profiles that resulted from $CH_2FH_4$ administration were not due to concurrent 5-FU dosing. The most recent exposure to 5-FU in these cases was slightly greater than a week prior to the study date, with the patients eligible, however, from the standpoint of toxicity evaluation to receive the weekly dose of 5-FU. Thus, residual FdUMP levels from previous exposure, below the detectable limits for assay, were expected to be present (See spears et al. Mol. Pharmacol. 27:302–07 (1985)). The serial biopsies were done following single dose administration of $CH_2FH_4$.

The formulation of $CH_2FH_4$ was as described in Example 2, and was performed on the day of $CH_2FH_4$ administration. The assays were also performed on the day of $CH_2FH_4$ administration.

The results in these patients of the pharmacodynamic tumor tissue analyses showed striking evidence of TS inhibition following $CH_2FH_4$ administration. These results are summarized in Tables II and III below.

TABLE II

TS INHIBITION AFTER $CH_2FH_4$ ADMINISTRATION

| PATIENT: | A.M.; last 5-FU treatment: ≧1 week |
|---|---|
| LOCATION: | Östra Sjukhuset (Eastern Hospital), Sweden |
| TUMOR: | Skin metastasis from gastric carcinoma |
| $CH_2FH_4$ FORMULATION: | 0.1M Na Ascorbate, pH <9.5, Sigma (6R,S)$CH_2FH_4$, DEAE-column purified |
| $CH_2FH_4$ DOSE: | 30 mg in 30 cc IV over 2 min; 4 mg as parent $CH_2FH_4$, 26 mg as $FH_4$. |

(Tumor Tissue Values = Ave. ± S.D.)

| Time of Biopsy[a] | THYMIDYLATE SYNTHASE (TS)[b] | | FBC[c] | |
|---|---|---|---|---|
| | pmol/g | % of Baseline | nmol/g | % of Baseline |
| 0 min | 1.31 ±0.13 | (100) | 5.88 +0.56 | (100) |
| 10 min | 0.26 ±0.17 | 19.8 | 0.23 +0.02 | 3.9 |
| 20 min | 0.56 ±0.06 | 42.7 | 0.27 +0.01 | 4.6 |
| 40 min | 0.99 ±0.08 | 75.6 | 0.21 | 3.6 |
| 60 min | 1.47 ±0.13 | 112.2 | 0.14 ±0.01 | 2.3 |

[a]Biopsies of solitary skin metastasis, average weight 68 ± 58 mg, time after $CH_2FH_4$ administration.
[b]By [6–$^3$H]FdUMP ligand-binding assay (CP Spears et al., Cancer Res. 42:450–56 (1982)).
[c]Folate Binding Capacity, FBC, is a measure of tissue $CH_2FH_4$ and $FH_4$ level (Invest. New Drugs 7:27–36 (1989), (modified after Priest et al., Biochem. J. 216:295–98 (1983)), with a Sigma (6R,S)-$CH_2FH_4$ standard value of 936 DPM/pmole.

TABLE III

TS INHIBITION AFTER $CH_2FH_4$ ADMINISTRATION

| PATIENT: | K.H.; last 5-FU treatment: ≧1 week |
|---|---|
| LOCATION: | Östra Sjukhuset (Eastern Hospital), Sweden |
| TUMOR: | Rectal adenocarcinoma, locally advanced |
| $CH_2FH_4$ FORMULATION[a]: | 0.2M Na Ascorbate, Sigma (6R,S)-$CH_2FH_4$ |
| $CH_2FH_4$ DOSE: | 35 mg IV over 1 min week #1; 50 mg IV in 40 ml week #2 |

(Tumor Tissue Values = Ave. ± S.D.)

| | THYMIDYLATE SYNTHASE (TS)[c] | | FBC[d] | |
|---|---|---|---|---|
| Time of Biopsy[b] | pmol/g Week #1 | % of Baseline Week #2 | ΔDPM Week #1 | % of Baseline Week #2 |
| 0 min | 5.77 (100) ±0.09 | 5.64 (100) ±1.26 | 759 (100) ±145 | 499 (100) ±190 |
| 10 min | 6.28 (212.4) ±1.92 | 10.25 (181.7) ±0.82 | 320 (42.2) ±60 | 376 (75.4) ±17 |
| 20 min | 2.26 (43.7) ±0.36 | 5.91 (104.8) ±0.17 | 314 (41.4) ±9 | 814 (163.1) |
| 30 min | 5.90 (114.1) ±0.12 | 2.02 (35.8) ±0.03 | 632 (83.3) ±26 | 249 (49.9) ±75 |
| 40 min | | 3.46 (61.3) ±0.28 | | 399 (80.0) ±44 |
| 24 hr | 6.32 (122.2) | | 1403 (184.8) | |

TABLE III-continued
TS INHIBITION AFTER CH₂FH₄ ADMINISTRATION

| PATIENT: | K.H.; last 5-FU treatment: ≧1 week |
|---|---|
| LOCATION: | Östra Sjukhuset (Eastern Hospital), Sweden |
| TUMOR: | Rectal adenocarcinoma, locally advanced |
| CH₂FH₄ FORMULATION[a]: | 0.2M Na Ascorbate, Sigma (6R,S)-CH₂FH₄ |
| CH₂FH₄ DOSE: | 35 mg IV over 1 min week #1; 50 mg IV in 40 ml week #2 |

(Tumor Tissue Values = Ave. ± S.D.)

| | THYMIDYLATE SYNTHASE (TS)[c] | | FBC[d] | |
|---|---|---|---|---|
| Time of Biopsy[b] | pmol/g Week #1 | % of Baseline Week #2 | ΔDPM Week #1 | % of Baseline Week #2 |
| | ±0.52 | | +130 | |

[a] On Week #1 the CH₂FH₄ was formulated at pH 2.0, DEAE-purified; On Week #2 the preparation was pH 9.0, with 6 mM (final concentration) CH₂O added, no DEAE step used.
[b] Biopsies of rectal pouch mass, average weights, 145 ± 39 mg (Week #1) and 136 ± 24 mg (Week #2). Time after CH₂FH₄ administration.
[c] By [6-³H]FdUMP ligand-binding assay (Spears et al., Cancer Res. 42:450-56 (1982)).
[d] Folate Binding Capacity, given in ΔDPM over [³H]FdUMP-TS binary complex background (Invest. New Drugs 7:27-36 (1989)); standard curve Sigma (6R,S)-CH₂FH₄ showed 920 and 898 ΔDPM/pmole for weeks 1 and 2. Multiply ΔDPM values by 0.0002 to convert to nmol/g.

In patient A. M., a sixty-seven year old woman with over a 3 year prior history of disseminated gastric cancer, and who was end-stage in her course, TS was inhibited 80.1 and 57.3% in her tumor at 10 and 20 min, respectively, in her tumor after CH₂FH₄ administration. (It should be noted that the CH₂FH₄ preparation was over 85% FH₄.) Notably, when she was studied again 2 weeks subsequently, with a repeat dose of CH₂FH₄, TS in the baseline tumor biopsy was undetectable (data not shown).

The FBC (folate binding capacity of L. casei TS-[3H]FdUMP added to the cytosols, (a measure of tissue CH₂FH₄ and FH₄, mostly presumed to be polyglutamates) also showed a surprising decrease, which continued through 60 min. Tissue FH₄ polyglutamates were not separately measured by use of CH20 addition to the FBC conditions. The continuing drop in FBC, however, at the 60-min time point rules out the possibility that all post-CH₂FH₄ biopsies were somehow an artifact of tumor tissue sampling. This paradoxical decrease in FBC is a characteristic feature of 5-FU-responding patients receiving high-dose LV added to 5-FU bolus i.v. therapy (C. P. Spears, et al. Presentation at 25th Annual Am. Soc. Clin. Oncol. meeting, May 22, 1989). This decrease was also seen in tumor of patient K. H. (Table 3). An explanation for the paradoxical decrease in FBC is that one-carbon exchange (e.g., R. G. Matthews et al, Adv. Enz. Regul. 26:157-70 (1987) occurred in the tumor tissue, between FH₄-monoglutamate derived within minutes from administration of the CH₂FH₄/FH₄ drug, and endogenous CH₂FH₄-polyglutamates. Since the polyglutamates of CH₂FH₄ may be expected to bind TS-FdUMP up to 50-fold more strongly than the monoglutamate (Houghton et al., Cancer Res. 48:3062-69 (1988)), the one-carbon exchange could lead to the observed decrease. This data is powerful evidence that CH₂FH₄/FH₄ given to this patient was rapidly transported and metabolized in her tumor. The decrease in TS in her tumor, then, is assumed to be related to this metabolism and the presence of non-measurable levels of FdUMP (at concentrations near stoichiometry with endogenous TS binding sites). The paradox of decreasing free TS with decreasing FBC also can be explained by metabolic channeling of administered CH₂FH₄ (Reddy et al., Proc. Natl. Acad. Sci. USA 77:3312-16, 1980), or by formation of TS-FdUMP-tetrahydrofolate, or of TS-deoxyuridylate-CH₂FH₄ ternary complexes by the unnatural (6S)-CH₂FH₄ or (6R)-FH₄ enantiomer, or by TS-FdUMP-CH₂FH₄ due to very rapid ternary complex formation (Lockshin et al., Biochem. Pharmacol. 30:247-57 (1981)) prior to the 10-min biopsy sample and one-carbon folate metabolism. In fact, the last explanation may be the most attractive, since the maximum TS inhibition was at this first biopsy time point. The degree of TS inhibition, 80.2% decrease over baseline value, and relatively limited duration of TS inhibition would predict that higher concentrations of FdUMP (as would result from 5-FU given shortly before, or with the CH₂FH₄) would lead to the desired therapeutic objective of complete TS inhibition.

In patient K. H., a fifty-five year old man with locally unresectable advanced rectal adenocarcinoma, the TS pharmacodynamic tumor tissue analyses were done twice, nine days apart. Following study, K. H. continued to receive intermittent bolus 5-FU. This patient had been previously a partial responder to 5-FU plus LV, with stable disease at the time of initial CH₂FH₄ administration. There were modifications of the CH₂FH₄ formulation between the 2 pharmacodynamic studies (See Table III). In the first study week, the pH was not adjusted up from 2.0, after DEAE column isolation of the Sigma (6R,S)-CH₂FH₄. Thus, some of this folate may also have been 5,10-methenyl-tetrahydrofolate. In the second study week, the pH was adjusted up to 9.0, and no DEAE step was used (with therefore 6 mM formaldehyde being present in the 40-cc volume for injection).

Patient K. H. showed changes in TS and in FBC assays after CH₂FH₄ administration that were qualitatively similar to those of Patient A.M., shown in Table III. Again, significant inhibition of TS over baseline values occurred in tumor samples after the CH₂FH₄ was given, in the absence of recent 5-FU exposure. On the first occasion, however, the pH of the formulation was low, and possibly the CH₂FH₄ was less well solubilized (or less stable, or both) than on Week #2, when an alkaline pH was used in addition to an excess of CH₂O. Comparison with patient A.M. suggests that the acute TS decrease resulted from FH₄ rather than CH₂FH₄. As in Patient A.M., TS inhibition, on both occasions, was transient, averaging 36 to 44% of baseline values for the combined data of the two studies, during the 20 to 30 min period after CH₂FH₄ was given. The most significant evidence of an increase in $CH_2FH_4$, as reflected by FBC assay, was at 24 hr after the first dose, which was expected on the basis of slow polyglutamation of folates generally. Significant drops in FBC also occurred in both weeks of study, again suggestive of the postulated one-carbon exchange between $FH_4$-monoglutamates and endogenous $CH_2FH_4$-polyglutamates. The fact of a less striking change in FBC values in tumor biopsies from K.H. than in A.M. is also consistent with the lower baseline FBC values (given in raw DPM, multiply by 0.0002 to convert to nmol/g units comparable to Patient A.M.), and the less striking but highly significant TS inhibition in tumor of K.H. As with Patient A.M., the data would predict, using purely kinetic arguments, that higher FdUMP levels generated from 5-FU given closer to the time of $CH_2FH_4$ dosing would lead to desired abrogation of TS activity.

It has long been known that FdUMP tends to persist at low levels in tissues following a single dose of 5-FU. FdUMP may therefore be slowly released from the RNA storage compartment inside cells.

Thus, because only trace concentrations of FdUMP are required to inhibit TS, if $CH_2FH_4$ or $FH_4$ levels are high, the TS inhibition observed in these two patients was likely to have been due to facilitation by the natural (6R)-$CH_2FH_4$ or (6S)-$FH_4$ enantiomers (diastereomers) of the $CH_2FH_4$ formulation on TS binding by residual FdUMP levels. These results suggest that repeated administration of $CH_2FH_4$ or $FH_4$ may be as effective as repeated dosing with 5-FU, but without the toxicity of dose-escalation of 5-FU.

The patients who received $CH_2FH_4$ showed no acute toxicities due to this treatment, including the instance of week #2 in K.H. when a slight excess of $CH_2O$ was present in the preparation. However, they did continue to manifest the same toxicities as their prior experience with 5-FU plus LV (i.e., mild nausea and fatigue). Patient A.M., as noted above, had extremely advanced gastric cancer at the time of the study and so was not evaluable for response. However, patient K.H. showed endoscopic evidence of continued disease stabilization if not at least additional, minor tumor regression noted over the subsequent months after the two weeks of $CH_2FH_4$ administration.

EXAMPLE 4

Figure 3:
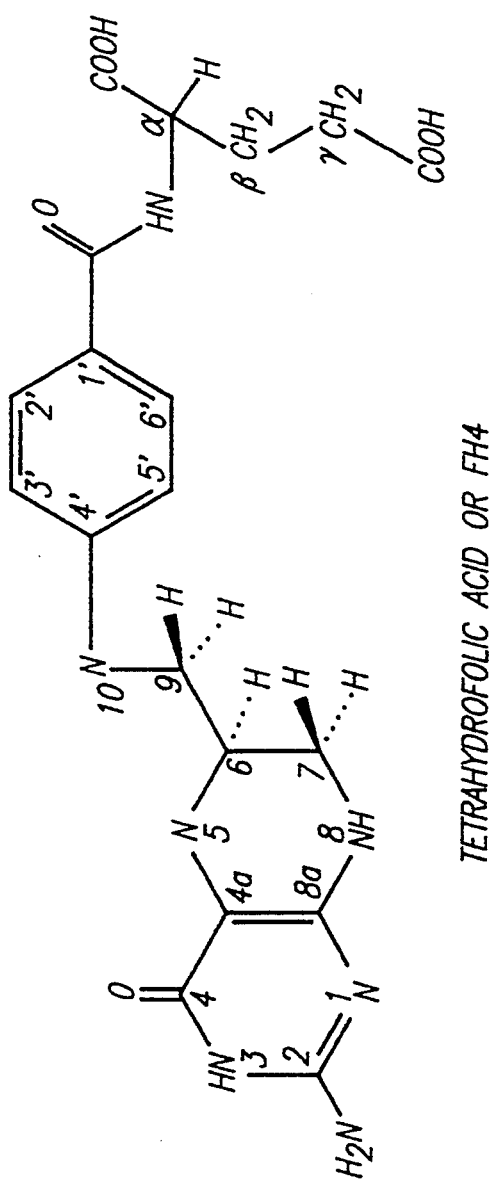
FIG. 3 represents the structure of tetrahydrofolic acid or $FH_4$, the predominant form at concentrations of less than 1 mM. The drawing represents either the (6R) or (6S) diastereomer.

(6R,S)-$FH_4$ Administration to Rats Bearing Transplanted Hepatic Colonic Carcinomas Table IV (below) shows the results of (6R,S)-$FH_4$ (see FIG. 3) administration to rats bearing transplanted hepatic colonic carcinoma. The present inventors have considerable experience with this model, and the antitumor effects of 5-FU shown are typical results, as are the TS and folate assays of control and 5-FU-only-treated rats. A striking finding was of growth stimulation yet decreased TS levels after (6R,S)-$FH_4$ alone. In fact, the "free TS" levels in the (6R,S)-$FH_4$-only-treated rats were the lowest of all arms of the study. This observation suggests that either the natural 6S-$FH_4$ or the unnatural 6R-$FH_4$ may have formed TS-inhibitory TS-dUMP-folate ternary complexes.

Alternatively, and more likely (since TS was assayed 24 h after drug exposure), (6R,S)-$FH_4$ caused decreases in TS levels on the basis of changes in gene regulation. Thus, the growth stimulation by $FH_4$ may have been by a purine pathway effect (vs. by TS which is the rate-limiting enzyme for pyrimidine pathway de novo DNA synthesis). These biochemical results are consistent with the inventors' hypothesis that (6R,S)-$FH_4$ potentiates 5-FU antitumor effect by increasing the degree of "unbalanced growth" resulting from TS inhibition in the face of on-going purine synthesis. In combination, the degree of synergy of (6R,S)-$FH_4$ with 5-FU in this example is greater than previously found for (6R,S)-leucovorin (Carlsson et al., Anticancer Res. 10:813–16 (1990)).

TABLE IV (6R,S)-TETRAHYDROFOLATE[a] AS A MODULATOR OF 5-FU IN AN EXPERIMENTAL LIVER CANCER IN RATS[b] RESULTS AT DAY 17 AFTER TRANSPLANTATION (Average of 3 rats/treatment)

| TREAT-MENT | TUMOR WEIGHT (g) | TS[d] (p mole/g) | 5,10-$CH_2FH_4$[d] (nmol/g) | $FH_4$[d] (nmol/g) |
|---|---|---|---|---|
| CONTROL | 5.84 | 18.96 | 0.69 | 1.18 |
| 5-FU ONLY (30 MG/KG) | 1.03 | 9.03 | 4.11 | 2.39 |
| 5-FU[c] + (6R,S)-$FH_4$[c] | 0.31 | 9.23 | 1.23 | 1.76 |
| (6R,S)-$FH_4$ only (30 mg/kg) | 10.43 | 7.13 | 2.93 | 2.31 |

[a] (6R,S)-$FH_4$ was the commercially available racemic tetrahydrofolate from Fluka Chemical Corp. (Cat. No. 87355, "Tetrahydrofolic acid dihydrochloride monohydrate," or "5,6,7,8-Tetrahydropteroyl-L-glutamic acid dihydrochloride monohydrate," >94% by HPLC). The (6 R,S)-$FH_4$ was weighed, dissolved in normal saline, and injected daily by tail vein administration using the air-free Protector device to prevent oxidative destruction of the folate.
[b] Inoculation of $1 \times 10^6$ viable colon tumor (nitrosoguanidine-induced) cells under the liver capsule on Day 1 (Carlsson et al., Anticancer Res. 10:813–16 (1990)). Animals sacrificed on Day 17 for excision of single liver tumor nodules for pharmacodynamic studies.
[c] 30 mg/kg
[d] Assays done as described (Spears et al. Adv. Exp. Med. Biol. 244:98–104 (1988)) and done at 24 h after last injection.

The above antitumor results have been confirmed in a separate experiment, using the same tumor line, dose, and route of administration of 5-FU and (6R,S)-$FH_4$ to 6 rats/group. Animals receiving (6R,S)-$FH_4$ alone showed tumor growth enhancement (171% of control tumor weight), to $6.0 \pm 1.1$ g, while the 5-FU+(6R,S)-$FH_4$ combination resulted in $0.70 \pm 0.10$ g size tumors.

EXAMPLE 5

Spontaneous Conversion of $CH_2FH_4$ to $FH_4$ by Dilution

Figure 4:
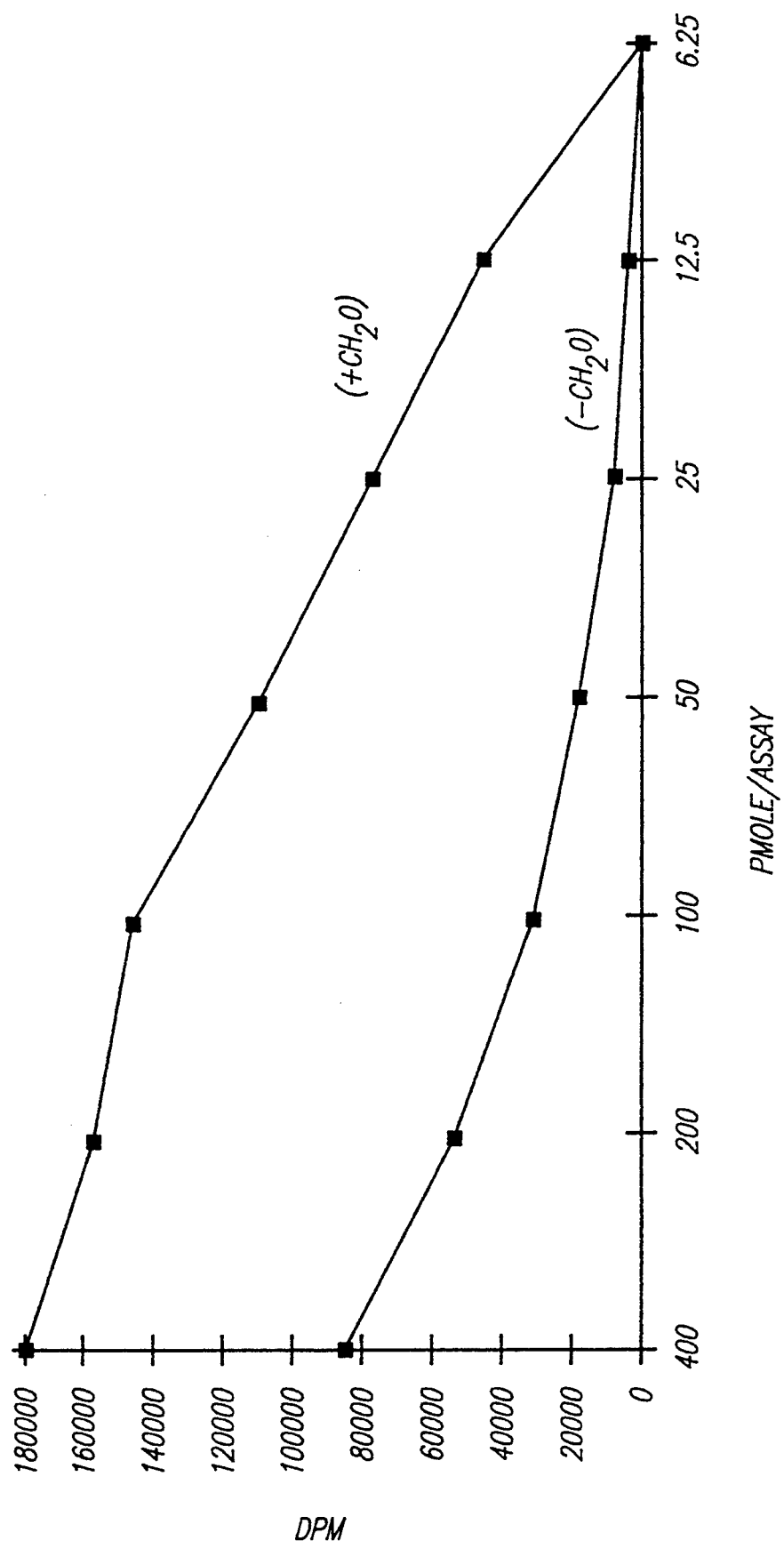
FIG. 4 shows the results of TS-[$^3$H]FdUMP-folate binding assay of $CH_2FH_4$ as a function of concentration of the folate in 0.2M Tris buffer, pH 7.4, with and without formaldehyde ($CH_2O$), 6 mM, addition.

FIG. 4 shows the results of TS-[$^3$H]FdUMP-folate binding assay of $CH_2FH_4$ as a function of concentration of the folate in 0.2M Tris buffer, pH 7.4, with and without formaldehyde ($CH_2O$), 6 mM, addition. The $CH_2FH_4$ was prepared as the racemic (6R, S) material from (6R, S)-$FH_4$ and excess formaldehyde, and DEAE-column isolation as described in FIG. 1. This preparation was essentially free of free formaldehyde based on colorimetric assay of bulk material (Nash, Biochem. J. 55:416–21 (1953)).

At all concentrations (total assays volume 150 μl ), excess formaldeyde was required to obtain maximal binding (which was still only 19.3% of stoichiometric binding). A notable effect was the increasing need for formaldehyde addition with increasing dilution, to obtain maximal $CH_2FH_4$ assay recovery.

This phenomenon has been a repeated observation in the laboratories of the inventors, and clearly shows that $CH_2FH_4$ on dilution becomes $FH_4$ with liberation of free formaldehyde (and formaldehyde solution intermediates such as $CH_2(OH)_2$). The concentration requirement for formaldehyde to reverse the $FH_4$ formation caused by dilution is in the millimolar range which is vastly higher than physiologic concentrations of formaldehyde (which possibly does not occur in any free state).

This requirement for a large excess of formaldehyde to shift the equilibrium between $FH_4$ and $CH_2FH_4$ (Eq. 1) was found by the inventors to $$CH_2FH_4 = FH_4 + CH_2O \quad \text{Eq. 1}$$

be independent of temperature, pH or the formaldehyde content of charcoal isolation, the presence of air exposure, or the presence of reducing agents. In addition, $[11\text{-}^{14}C]CH_2FH_4$ prepared as described (Moran et al., Proc. Natl. Acad. Sci. USA 76:1456-60 (1979)), and DEAE-purified (as the concentrated material) of excess $^{14}CH_2O$, was confirmed to have a labile $^{14}CH_2O$ group by dimedone trapping. For instance, 46,664 DPM of $[11\text{-}^{14}C]\text{-}CH_2FH_4$ diluted to 1 ml in $H_2O$ was found to have 67.8% of the label recoverable by chloroform extraction of dimedone (methone) product (37° C.).

EXAMPLE 6

Pharmacologically Mediated Decreases in Intratumoral $FH_4$ in Patients Receiving 5-FU Plus High Dose (6R,S)-Leucovorin are Associated with Rapid Reversal of Antitumor Effects As noted previously (see pages 5-6) and mentioned in C. P. Spears, et al., Proc. Am. Soc. Clin. Oncol. 8:69 (1989), the inventors have used pharmacologic intervention to convert intracellular $FH_4$ to $CH_2FH_4$ in patients receiving high-dose reduced folate therapy combined with weekly i.v. bolus 5-FU, 450 mg/sq. m. The method used was administration of i.v. L-serine, 15.0 grams, over 1 hour after the end of overnight high-dose (6R,S)-leucovorin i.v. infusion.

In contrast to the data shown in Tables II and III, the inventors were able to also assay for intratumoral $FH_4$ in addition to $CH_2FH_4$ (this latter is also referred to as "FBC" in those Tables or Folate-Binding Capacity), at time points during this pharmacologic forcing of metabolism of $FH_4$ to $CH_2FH_4$ through the enzyme, serine hydroxymethyltransferase. This enzyme splits a carbon of L-serine to generate formaldehyde in the presence of $FH_4$.

Table V below details the results of pharmacodynamic studies in 2 patients (at Norris-USC Comprehensive Cancer Center, Los Angeles).

TABLE V

| | TIME[a] (min) | $CH_2FH_4$ | $FH_4$[b] | RATIO[c] | CLINICAL EFFECT |
|---|---|---|---|---|---|
| Patient | 0 | 0.194 | 2.370 | 12.2 | Accelerated |

Effects of Conversion of $FH_4$ to $CH_2FH_4$ in Breast Cancer Biopsies

TABLE V-continued

Effects of Conversion of $FH_4$ to $CH_2FH_4$ in Breast Cancer Biopsies

| | TIME[a] (min) | $CH_2FH_4$ | $FH_4$[b] | RATIO[c] | CLINICAL EFFECT |
|---|---|---|---|---|---|
| H.S.[d] | 22 | 0.253 | 0.854 | 3.4 | progression of |
| | 65 | 0.340 | 0.907 | 2.7 | tumor growth |
| Patient | 0 | 0.265 | 1.943 | 7.3 | Accelerated |
| M.H.[e] | 25 | 0.396 | 1.128 | 2.9 | progression of |
| | 82 | 0.475 | 1.420 | 3.0 | tumor growth |

[a]Minutes after initiation of 15.0-gram L-Serine i.v. 60-min infusion, after end of overnight (6R,S)-leucovorin high-dose i.v. infusion.
[b]Assays performed as described (C.P. Spears et al., Adv. Exp. Med. Biol. 244:97-106, 1988).
[c]Ratio of $FH_4/CH_2FH_4$.
[d]A 74-year-old woman with advanced chest-wall infiltrating breast carcinoma metastases, with stable disease activity on weekly 5-FU plus high-dose (6R,S)-leucovorin.
[e]A 43-year old woman with advanced chest-wall metastases who has previously experienced a minimal response to weekly 5-FU plus high-dose (6R,S)-leucovorin.

Similarly, in a third patient (a 42-year old woman with extensive bone and soft tissue metastases in whom no biopsies were taken), L-serine i.v. infusion added to 5-FU/(6R,S)-leucovorin treatment resulted in rapid acceleration of objective tumor growth and tumor symptoms. Subsequently, in order to reverse the folate conversion, toward $FH_4$ by glycine administration, 10 grams i.v., this patient then had a rapid response to 5-FU therapy. The present inventors have previously shown the effectiveness of glycine in promoting $FH_4$ production from $CH_2FH_4$ (Spears et al., Pteridines and Folic Acid Derivatives, (Curtius, H.-C., et al., eds.) Walter de Gruyter, Berlin, pp. 811-816 (1990). Glycine acts as a trap for the methylene (formaldehyde unit) of $CH_2FH_4$ in the presence of serine hydroxymethyltransferase, by converting the formaldehyde to the 3-carbon of L-serine.

This example supports the hypothesis that an objective of (6R,S)-$CH_2FH_4$ administration is expansion of pools of $FH_4$ (and its polyglutamates), and of increased ratios of $FH_4/CH_2FH_4$.

EXAMPLE 7

Cell Culture Study Comparing Relative Effectiveness of Different Folate Forms on Assayed Intracellular Levels Of $CH_2FH_4$ and $FH_4$ In further support of the hypothesis that objectives of $CH_2FH_4$ administration are increases in $FH_4$ and $FH_4/CH_2FH_4$ values, are the results of a cell culture study, shown in Table VI, comparing the relative effectiveness of different folate forms on assayed intracellular levels of the two folates. Each folate form was dosed at 10 μM in the natural diastereomer (enantiomer or diastereomer). The (6R)-$CH_2FH_4$ (natural diastereomer) was free of excess formaldehyde, and studied for only a 90-min effect vs. 16-hr for the other folates because of its lower extracellular stability.

TABLE VI $CH_2FH_4$ and $FH_4$ Levels In CCRF-CEM Cells After 16-hr Exposure to 10 μM Folate: Comparison of Sources (Intracellular Folates In nmole/$10^9$ Cells, AVE ± S.D.

| | CONTROL | (6R,S)-MTHF[a] | (6S)-LV[b] | DHF[c] | (6R)-$CH_2$—$FH_4$[d] |
|---|---|---|---|---|---|
| $CH_2FH_4$ | 0.04 | 0.51 | 0.13 | <0.02 | 0.19[a] |
| | ±0.01 | ±0.07 | ±0.02 | ±0.01 | ±0.02 |
| $FH_4$ | 3.08 | 10.55 | 10.64 | 7.10 | 8.81[a] |

TABLE VI-continued $CH_2FH_4$ and $FH_4$ Levels In CCRF-CEM Cells After 16-hr Exposure to 10 μM Folate: Comparison of Sources (Intracellular Folates In nmole/$10^9$ Cells, AVE ± S.D.

| CONTROL | (6R,S)-MTHF[a] | (6S)-LV[b] | DHF[c] | (6R)-$CH_2$—$FH_4$[d] |
|---|---|---|---|---|
| ±0.13 | ±0.59 | ±0.25 | ±0.01 | ±0.39 |

[a]Racemic methyltetrahydrofolate, 10 μM in each diastereomer.
[b]Natural (6S)-leucovorin.
[c]Dihydrofolate.
[d]The natural diastereomer, prepared as described in Example 1. Results represent values at 90 min of exposure.

Two observations are most notable in Table VI: (a) the brief (90 min) (6R)-$CH_2FH_4$ exposure was as effective as 16-hr exposure to the other folates, and (b) the major effect of (6R)-$CH_2FH_4$ exposure was to increase $FH_4$ and $FH_4$/$CH_2FH_4$ levels, with only a minor effect on $CH_2FH_4$ levels per se.

EXAMPLE 8

Comparison of Natural (6R)-$CH_2FH_4$ and Unnatural (6S)-$CH_2FH_4$ Diastereomers A study has been completed, for comparison of natural (6R)-$CH_2FH_4$ and unnatural (6S)-$CH_2FH_4$ diastereomers. The preparation of the two forms was done as described by Kisliuk, et al., Cancer Treat. Rep. 61:647–50 (1977), using DEAE-cellulose column chromatography, with elution by potassium bicarbonate buffer. The two separate major peaks were individually pooled, lyophilized to dryness, and used for injection. As in the original detailed description of the method of Kisliuk, et al. (Biochem. 20:929–934), the methylene content was substoichiometric with tetrahydrofolate ($FH_4$). That is, methylene units were present in apparently lower concentration than $FH_4$ concentrations.

Rats bearing the transplanted colon cancer, as described in Example 4 and in Carlsson, et al., Anticancer. Res. 10:813–816, 1991, were treated with either the (6R)-$CH_2FH_4$ or the (6S)-$CH_2FH_4$, formulated and injected according to the methods described in Table IV, except that the injected amounts were 15 mg/kg per dose.

At Day 17, the rats were sacrificed, and the tumors were measured for both volume end weight. Volumes were calculated by the equation for an ellipsoid in revolution, $V=(4/3)\pi ab^2$ were a=the long diameter/2 and b=the perpendicular short diameter/2.

Figure 5:
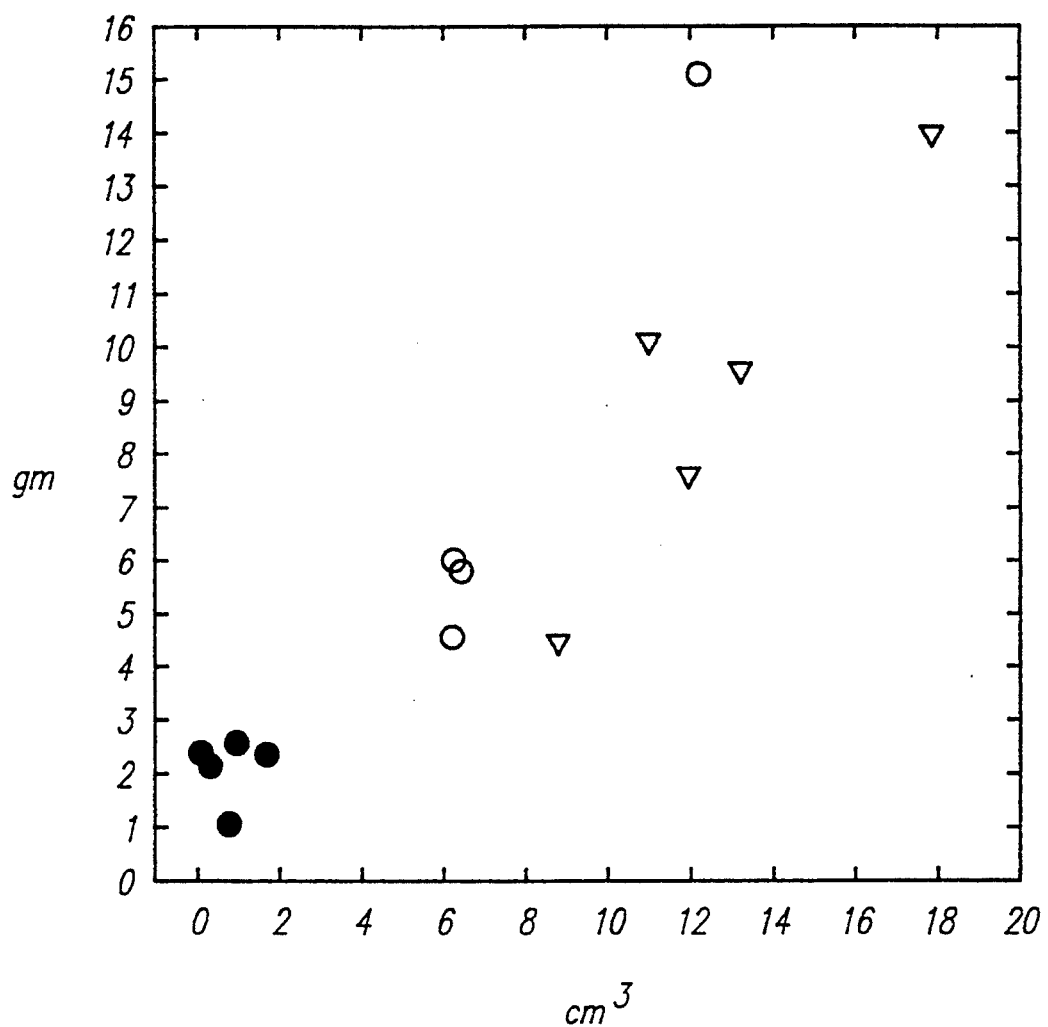
FIG. 5 shows the results of an experiment comparing the effects of natural (6R)-$CH_2FH_4$ versus unnatural (6S)-$CH_2FH_4$ on rats bearing transplanted colon cancer. The filled circles are the weights and volumes of tumors of rats treated with the unnatural (6S)-$CH_2FH_4$ diastereomer (mostly (6R)-$FH_4$ material). The triangles are results for the natural (6R)-$CH_2FH_4$ (mostly (6S)-$FH_4$), and the open circles, non-treated tumors. It should be emphasized that no fluorinated pyrimidine was used, just the folate injections.

FIG. 5 shows the individual tumor results of this experiment. The filled circles are the weights and volumes of tumors of rats treated with the unnatural (6S)-$CH_2FH_4$ diastereomer (mostly (6R)-$FH_4$ material in dilute solution and blood); the triangles are results for the natural (6R)-$CH_2FH_4$ (mostly (6S)-$FH_4$); and the open circles, control non-treated tumors. It is emphasized here that no fluorinated pyrimidine was used, just the folate injections. The average values (±S. E.) of these data were presented in Table VII.

Table VII

| Folate | Weight ± SE | P-Value* | Volume ± SE | P-Value* |
|---|---|---|---|---|
| Control | 7.93 ±2.42 | — | 7.81 ±0.15 | — |
| (6S)-$CH_2FH_4$ [a] (Unnatural) (15 mg/kg) | 2.14 ±0.27 | <0.001 | 0.74 ±0.29 | <0.03 |
| (6R)-$CH_2FH_4$ [b] (Natural) (15 mg/kg) | 9.11 ±1.56 | 0.6 | 12.58 ±1.49 | <0.046 |

*Comparision with control rats, based on differences between the means.
[a]No cofactor activity by L. casei/dUMP spectrophotometric assay; TS-[$^3$H]FdUMP-folate ternary complex formation without formaldehyde addition was 38.5% of the value for the natural (6R)-$CH_2FH_4$ with 6 mM formaldehyde added. (About 1 pmole of parent $CH_2FH_4$ was needed in the binding assay.) Furthermore, this unnatural folate showed decreases in TS-[$^3$H]FdUMP complex background on addition of formaldehyde (6 mM), which is a striking kinetic difference from the natural form of $CH_2FH_4$.
[b]Only 11.8 ± 7.9% of maximal L. casei TS-[$^3$H]FdUMP-folate ternary complex formation (using 6 mM formaldehyde concentration) which is consistent with ternary complex formation by (6S)-$FH_4$ alone.

In view of the results of Table VII, it is clear that the racemic mixture of (6R,S)-$CH_2FH_4$, which is predominantly (6R, S)-$FH_4$ in dilute solution, has antitumor activity by two different mechanisms: the unnatural (6R)-$FH_4$ (in solution; (6S)-$CH_2FH_4$ as the parent powder with substoichiometric methylene) diastereomer has direct tumor-growth-inhibitory activity; the natural (6S)-$FH_4$ (in solution, (6R)-$CH_2FH_4$ as the parent powder) potentiates fluorinated pyrimidine action by TS-FdUMP-$FH_4$ ternary complex formation (TS-inhibition) in the face of purine and RNA growth stimulation with promotion of unbalanced growth.

EXAMPLE 9

Effect of the Unnatural Diastereomer (6S)-$CH_2FH_4$ on Human Lymphoblast Cells

The unnatural diastereomer, (6S)-$CH_2FH_4$ prepared by DEAE-column, potassium bicarbonate separation from the natural diasteromer as described in Example 8, was dissolved in 0.2M Tris-HCl buffer, pH 7.0, containing sodium ascorbate (100 mM) and 2-mercaptoethanol. This preparation was from the same lot of material described in Example 8. As noted in the footnote of Table VII, in the absence of supplemental formaldehyde, the yield of dextrancharcoal isolated complex was 38.5% of the value for the natural (6R)-$CH_2FH_4$ (with added 6 mM formaldehyde). The presence of formaldehyde actually decreased the yield of TS-[3H]FdUMP-ternary complex of the unnatural diastereomer to 23.3%. This behavior of the unnatural diastereomer is exactly opposite to that of natural (6R)-$CH_2FH_4$ which becomes (6S)-$FH_4$ on dilution and shows a striking increase in TS-[$^3$H]FdUMP-folate yield on formaldehyde added in great excess.

Separate cultures tubes at 37° C. with 1 ml each of CCRF-CEM human lymphoblast cells, 4.6×$10^5$ cells/ml, in exponential log phase growth were exposed to the unnatural diastereomer, (6R)-$FH_4$ (made up from (6S)-$CH_2FH_4$, 1.56 mM stock solution, with 32 microliters added to each ml of cells), 48 μM final concentration. Cells were incubated for 30, 60, and 120 minutes of drug exposure, prior to addition of [5-$^3$H]deoxyuridine (150,000 CPM of approx. 18–20 Ci/mmo. spec. act.) and 10 min. 37° C. incubation prior to 3% charcoal addition for isolation of tritiated water. The amount of tritiated water is proportional to the activity of TS in the intact cells (N. Kundu et al., *J. Med. Chem.* 33:1975–79 (1990)).

Control cells, without (6R)-FH$_4$/(6S)-CH$_2$FH$_4$ exposure showed minimal increases over the 2 hour time period consistent with cell growth: 2566, 2662, and 2902 CPM at 30, 60 and 120 min.

The CCRF-CEM cells exposed to 48 μM (6R)-FH$_4$/(6S)-CH$_2$FH$_4$ showed striking TS-inhibition; values of tritiated water production were 2004, 1750, and 1146 CPM at 30, 60 and 120 min. of drug exposure. These values are 78.1%, 65.7% and 39.5% of those of the control, untreated cells. Thus, inhibition of TS activity in intact cells was 60.5% by the two hour time point of drug exposure.

The inventors believe that these results indicate that the unnatural folate caused TS inhibition. The time course of progressive TS inhibition was consistent with increasing intracellular polyglutamation of the (6R)-FH$_4$/(6S)-CH$_2$FH$_4$ folate with increasing affinity for binding to and inactivating TS inside the cells. This possibility was suggested in Example 3 as an explanation for TS inhibition in a patient's tumor after (6R,S)-CH$_2$FH$_4$ (predominantly (6R,S)-FH$_4$ in solution) administration. Polyglutamates of the unnatural (6R)-FH$_4$ have been reported in a purely cell-free kinetic study (Kisliuk et al., *J. Biol. Chem.* 249:4100–03 (1974)) to be stronger TS inhibitors than the monoglutamate, and any oxidation of these folates to their dihydrofolate polyglutamates would also be expected to inhibit TS (Lockshin et al., *J. Biol. Chem.* 254:12285–88 (1979)).

We claim:

1. A composition comprising (6R,S)-FH$_4$ and 5-FU in amounts effective in combination to achieve substantially complete inhibition of thymidylate synthase (TS), together with a pharmaceutically acceptable carrier.

2. The composition of claim 1 further comprising an agent that stabilizes FH$_4$.

3. The composition of claim 2 wherein the agent that stabilizes FH$_4$ is an ascorbate salt.

4. The composition of claim 2 wherein the agent that stabilizes FH$_4$ is reduced glutathione.

5. The composition of claim 2 wherein the agent that stabilizes FH$_4$ is formaldehyde.

6. In a method of inhibiting the growth of a tumor in a patient by administering 5-FU to said patient, the improvement comprising administering (6R,S)-tetrahydrofolate (FH$_4$) in an amount sufficient in combination with the 5-FU as active agents to achieve substantially complete inhibition of thymidylate synthase (TS) in a patient with a tumor sensitive to said combination of active agents.

7. The method of claim 6 wherein FH$_4$ is administered to said patient by protracted, continuous intravenous infusion through a central venous catheter.

8. The method of claim 6 wherein FH$_4$ is administered to said patient concurrently with 5-FU.

9. The method of claim 6 wherein FH$_4$ is administered to said patient prior to the administration of 5-FU.

10. The method of claim 9 wherein FH$_4$ is administered to said patient 6–24 hours prior to the administration of 5-FU.

11. The method of claim 9 wherein FH$_4$ is administered to said patient 1–3 hours prior to the administration of 5-FU.

12. The method of claim 6 wherein FH$_4$ is administered to said patient subsequent to the administration of 5-FU.

13. The method of claim 12 wherein FH$_4$ is administered to said patient 1–10 days subsequent to the administration of 5-FU.

14. The method of claim 12 wherein FH$_4$ is administered to said patient 1–6 hours subsequent to the administration of 5-FU.

15. The method of claim 6 wherein FH$_4$ is administered to said patient intravenously, intraarterially or intraperitoneally.

16. The method of claim 15 wherein FH$_4$ is administered in a dosage of 5–500 mg/m$^2$.

17. The method of claim 16 wherein FH$_4$ is administered in a dosage of 20–200 mg/m$^2$.

18. The method of claim 16 wherein FH$_4$ is administered intravenously.

19. The method of claim 18 wherein FH$_4$ is administered to said patient every 4–6 hours.

20. The method of claim 18 wherein FH$_4$ is administered to said patient once daily.

21. The method of claim 18 wherein FH$_4$ is administered to said patient once weekly.

22. The method of claim 19 wherein FH$_4$ is administered prior to the administration of 5-FU.

23. The method of claim 19 wherein FH$_4$ is administered subsequent to the administration of 5-FU.

24. The method of claim 20 wherein FH$_4$ is administered to said patient through a central venous catheter.

25. The method of claim 6 wherein the concentration of FH$_4$ administered is from 0.1 to 20 mg/ml in alkaline vehicles.

26. The method of claim 6 wherein the concentration of FH$_4$ administered is from 0.1 to 10 mg/ml in physiologic saline.

* * * * *